US008445841B2

(12) United States Patent
Szobota et al.

(10) Patent No.: US 8,445,841 B2
(45) Date of Patent: May 21, 2013

(54) METHOD AND APPARATUS FOR A MID-INFRARED (MIR) SYSTEM FOR REAL TIME DETECTION OF PETROLEUM IN COLLOIDAL SUSPENSIONS OF SEDIMENTS AND DRILLING MUDS DURING DRILLING OPERATIONS, LOGGING AND PRODUCTION OPERATIONS

(75) Inventors: John S. Szobota, Morristown, NJ (US);
James M. Brown, Flemington, NJ (US);
Clifford C. Walters, Milford, NJ (US);
Mark M. Disko, Glen Gardaen, NJ (US); Boris Mizaikoff, Ulm (DE)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 13/314,423

(22) Filed: Dec. 8, 2011

(65) Prior Publication Data

US 2012/0170023 A1 Jul. 5, 2012

Related U.S. Application Data

(60) Provisional application No. 61/429,637, filed on Jan. 4, 2011.

(51) Int. Cl.
*G01V 5/04* (2006.01)
(52) U.S. Cl.
USPC ........................................................ 250/254
(58) Field of Classification Search
USPC ................. 250/253, 254, 255, 256, 262, 263, 250/269.1; 356/51
See application file for complete search history.

(56) References Cited

U.S. PATENT DOCUMENTS

| | | | |
|---|---|---|---|
| 5,306,909 A | 4/1994 | Jones et al. | 250/255 |
| 5,898,517 A | 4/1999 | Weis | |
| 6,292,756 B1 | 9/2001 | Lievois et al. | 702/50 |
| 6,507,401 B1 | 1/2003 | Turner et al. | 356/436 |

(Continued)

FOREIGN PATENT DOCUMENTS

| | | |
|---|---|---|
| GB | 2408796 A | 6/2005 |
| WO | WO 2005/088270 A2 | 9/2005 |
| WO | WO 2005/088270 A3 | 9/2005 |
| WO | WO 2007/143474 A1 | 12/2007 |

OTHER PUBLICATIONS

M. Janotta, A. Katzir, B. Mizaikoff; "Sol-Gel-Coated Mid-Infrared Fiber-Optic Sensors"; Applied Spectroscopy, vol. 57, No. 7, 2003, pp. 823-828.

(Continued)

*Primary Examiner* — Mark R Gaworecki
(74) *Attorney, Agent, or Firm* — David M. Weisberg

(57) ABSTRACT

A first waveguide has a top face positioned in an oil well borehole for wetting by returning drilling mud from a drill bit as drilling progresses. A second waveguide is positioned in the borehole for wetting by new drilling mud being pumped to the drill bit. MIR light rays are fed from an MIR light source into the first and second waveguides for causing evanescent waves to be generated by each waveguide for reacting with the molecules of the associated drilling mud, respectfully, whereby a modulated optical signal representative of spectra of components and particles in the associated drilling mud, respectively, are emitted from each waveguide. The modulated optical signals are converted to electrical signals, subtracted from one another to remove common mode signals, and passed into a processor programmed for extracting the spectra hydrocarbon components contained in the returning drilling mud as the result of the drilling activity.

66 Claims, 17 Drawing Sheets

U.S. PATENT DOCUMENTS

| | | |
|---|---|---|
| 6,683,681 B2 | 1/2004 | DiFoggio et al. ............. 356/128 |
| 6,707,556 B2 | 3/2004 | Turner et al. .................. 356/436 |
| 7,081,615 B2 | 7/2006 | Betancourt et al. ........... 250/255 |
| 7,095,012 B2 | 8/2006 | Fujisawa et al. ........... 250/269.1 |
| 7,173,239 B2 | 2/2007 | DiFoggio .................... 250/269.1 |
| 7,195,063 B2 | 3/2007 | Nogueira et al. ............. 166/264 |
| 7,196,786 B2 | 3/2007 | DiFoggio ...................... 356/301 |
| 7,231,819 B2 | 6/2007 | Jones et al. ................. 73/152.23 |
| 2006/0142955 A1 | 6/2006 | Jones et al. ...................... 702/32 |
| 2007/0013911 A1 | 1/2007 | DiFoggio |
| 2007/0062272 A1 | 3/2007 | Frechin et al. ............. 73/152.04 |
| 2009/0180101 A1 | 7/2009 | Csutak .......................... 356/70 |
| 2009/0206242 A1 | 8/2009 | Mizaikoff et al. ........ 250/227.11 |
| 2010/0177310 A1 | 7/2010 | Difoggio |

OTHER PUBLICATIONS

M. Janotta, M. Karlowatz, F. Vogt, B. Mizaikoff; "Sol-gel Based Mid-Infrared Evanescent Wave Sensors for Detection of Organophosphate Pesticides in Aqueous Solution"; Analytica Chimica Acta, Elsevier, vol. 496, 2003, pp. 339-348.

G. T. Dobbs, B. Balu, C. Young, C. Kranz, D. W. Hess, B. Mizaikoff; "Mid-Infrared Chemical Sensors Utilizing Plasma-Deposited Fluorocarbon Membranes"; Analytical Chemistry, vol. 79, No. 24, Dec. 15, 2007, pp. 9566-9571.

B. Mizaikoff, R. Göbel, R. Krska, K. Taga, R. Kellner, M. Tacke, A. Katzir; "Infrared Fiber-Optical Chemical Sensors With Reactive Surface Coatings"; Sensors and Actuators B, Elsevier, vol. 29, pp. 58-63, 1995.

M. Karlowatz, M. Kraft, B. Mizaikoff; "Simultaneous Quantitative Determination of Benzene, Toluene and Xylenes in Water Using Mid-Infrared Evanescent Field Spectroscopy"; Analytical Chemistry, vol. 76, No. 9, 2004, pp. 2643-2648, with supporting Information for Manuscript, pp. S1-S5.

C. Charlton, M. Giovannini, J. Faist, B. Mizaikoff; "Fabrication and Characterization of Molecular Beam Epitaxy Grown Thin-Film GaAs Waveguides for Mid-Infrared Evanescent Field Chemical Sensing"; Analytical Chemistry, vol. 78, No. 12, Jun. 15, 2006, pp. 4224-4227.

S.-S. Kim, C. Young, B. Mizaikoff; "Miniaturized Mid-Infrared Sensor Technologies"; Anal. Bioanal. Chem., vol. 390, 2008, pp. 231-237.

J. F. Kastner, M. Tacke, A. Katzir, B. Mizaikoff, R. Göbel, R. Kellner; "Optimizing the Modulation for Evanescent Wave Analysis with Laser Diodes (EWALD) for Monitoring Chlorinated Hydrocarbons in Water"; Sensors and Actuators B, Elsevier, vol. 38-39, 1997, pp. 163-170.

M. Jakusch, B. Mizaikoff, R. Kellner, A. Katzir; "Towards a Remote IR Fiber-Optic Sensor System for the Determination of Chlorinated Hydrocarbons in Water"; Sensors and Actuators B, vol. 38-39, 1997, pp. 83-87.

B. Mizaikoff, "Mid-Infrared Evanescent Wave Sensors—A Novel Approach for Subsea Monitoring", Meas. Sci. Technol. vol. 10 Page, 1999, pp. 1185-1194.

M. Jakusch, M. Janotta, B. Mizaikoff, K. Mosbach, K. Haupt; "Molecularly Imprinted Polymers and Infrared Evanescent Wave Spectroscopy. A Chemical Sensors Approach"; Analytical Chemistry, vol. 71, No. 20, Oct. 15, 1999 pp. 4786-4791.

M. Kraft, B. Mizaikoff; "A Mid-Infrared Sensor for Monitoring of Chlorinated Hydrocarbons in the Marine Environment"; Intern. J. Environ. Anal. Chem., vol. 78 (3-4), 2000, pp. 367-383.

M. Karlowatz, M. Kraft, E. Eitenberger, B. Mizaikoff, A. Katzir; "Chemically Tapered Silver Halide Fibers: An Approach for Increasing the Sensitivity of Mid-Infrared Evanescent Wave Sensors"; Applied Spectroscopy, vol. 54, No. 11, 2000, pp. 1629-1633.

H. Steiner, M. Jakusch, M. Kraft, M. Karlowatz, T. Baumann, R. Niessner, W. Konz, A. Brandenburg, K. Michel, C. Boussard-Plédel, B. Bureau, J. Lucas, Y. Reichlin, A. Katzir, N. Fleischmann, K. Staubmann, R. Allabashi, J. M. Bayona, and B. Mizaikoff; "In-Situ Sensing of Volatile Organic Compounds in Groundwater: First Field Tests of a Mid-Infrared Fiber-Optic Sensing System"; Applied Spectroscopy, vol. 57, No. 6, 2003, pp. 607-613.

B. Mizaikoff, "Mid-IR Fiber-Optic Sensors"; Analytic Chemistry, vol. 75, Jun. 1, 2003, pp. 258A-267A.

T. Beyer, P. Hahn, S. Hartwig, W. Konz, S. Scharring, A. Katzir, H. Steiner, M. Jakusch, M. Kraft, B. Mizaikoff; "Mini Spectrometer with Silver Halide Sensor Fiber for In-Situ Detection of Chlorinated Hydrocarbons"; Sensors and Actuators B, Elsevier, vol. 90, 2003, pp. 319-323.

F. Vogt, M. Karlowatz, M. Jakusch, B. Mizaikoff; "The Automated Sample Preparation System MixMaster for Investigation of Volatile Organic Compounds with Mid-Infrared Evanescent Wave Spectroscopy"; The Royal Society of Chemistry, Analyst, vol. 128, 2003, pp. 397-403.

H. Steiner, K. Staubmann, R. Allabashi, N. Fleischmann, A. Katzir, Y. Reichlin, B. Mizaikoff; "Online Sensing of Volatile Organic Compounds in Groundwater using Mid-Infrared Fibre Optic Evanescent Wave Spectroscopy: A Pilot Scale Test"; Water Science and Technology, vol. 47, No. 2, 2003, pp. 121-126.

B. Mizaikoff, "Infrared Optical Sensors for Water Quality Monitoring"; Water Science and Technology, vol. 47, 2003, pp. 35-42.

M. Kölhed, M. Haberkorn, V. Pustogov, B. Mizaikoff, J. Frank, B. Karlberg, B. Lendl; "Assessment of Quantum Cascade Lasers as Mid Infrared Light Sources for Measurement of Aqueous Samples"; Vibrational Spectroscopy, vol. 29, 2002 pp. 283-289.

L. Hvozdara, N. Pennington, M. Kraft, M. Karlowatz, B. Mizaikoff; "Quantum Cascade Lasers for Mid-Infrared Spectroscopy"; Vibrational Spectroscopy, vol. 30, 2002, pp. 53-58.

M. Kraft, M. Karlowatz, B. Mizaikoff, R. Stück, M. Steden, M. Ulex, H. Amann; "Sensor Head Development for Mid-Infrared Fibre-Optic Underwater Sensors"; Measurement Science and Technology, vol. 13, 2002, pp. 1294-1303.

M. Kraft, M. Jakusch, M. Karlowatz, A. Katzir, B. Mizaikoff; "New Frontiers for Mid-Infrared Sensors Towards Deep Sea Monitoring with a Submarine FT-IR Sensor System"; Applied Spectroscopy, vol. 57, No. 6, 2003, pp. 591-599.

Z. Ge, C. W. Brown, J. J. Alberts; "Infrared Fiber Optic Sensor for Petroleum"; Environmental Science & Technology, vol. 29, No. 4, 1995, pp. 878-882.

R. P. McCue, J. E. Walsh, F. Walsh, F. Regan; "Environmental Sensing of Hydrocarbons in Water Using Mid-Infrared Optical Fibres", Proceedings of SPIE, vol. 4876, 2003 pp. 952-957.

R. P. McCue, J. E. Walsh, F. Walsh, F. Regan; "Modular Fiber Optic Sensor for the Detection of Hydrocarbons in Water"; Sensors and Actuators B, Elsevier, vol. 114, 2006, pp. 438-444.

A. Silva, M. Pimentel, I. M. Raimundo, Jr., Y. M.B. Almeida; "Effect of Plasticizers on a PVC Sensing Phase for Evaluation of Water Contamination By Aromatic Hydrocarbons and Fuels Using Infrared Spectroscopy"; Sensors and Actuators B, Elsevier, vol. 139, 2009, pp. 222-230.

B. Pejcic, M. Myers, and A. Ross; "Mid-Infrared Sensing of Organic Pollutants in Aqueous Environments"; Sensors, 9, 2009, pp. 6232-6253.

P. Hahn, M. Tacke, M. Jakusch, B. Mizaikoff, O. Spector, and A. Katzir: "Detection of Hydrocarbons in Water by MIR Evanescent-Wave Spectroscopy with Flattened Silver Halide Fibers"; Applied Spectroscopy, vol. 55, No. 1, 2001, pp. 39-43.

N. Afanasyeva, S. Kolyakov, R. Bruch, S. Gummuluri; "Biomedical, Environmental and Industrial Application of Fiberoptical Infrared Spectroscopy"; SPIE vol. 4129, 2000, pp. 272-283.

J. F. Kastner, M. Tacke; "EWALD: Detection of Hydrocarbons in Water by Evanescent Wave Analysis with Laser Diodes"; VDI-Berichte, (5th International Symposium on Gas Analysis by Tunable Diode Lasers 1998), vol. 1366, 1998, pp. 47-58.

M. Blanco, J. Coello, H. Iturriaga, S. Maspoch, and R. González; "Determination of Water in Lubricating Oils by Mid-and Near-Infrared Spectroscopy"; Mikrochimica Acta, vol. 128, 1998 pp. 235-239.

R. Kellner, R. Göbel, R. Götz, B. Lendl, B. Edl-Mizaikoff, M. Tacke, A. Katzir; "Recent Progress on MID-IR Sensing with Optical Fibers"; SPIE vol. 2508, (Chemical, Biochemical, and Environmental Fiber Sensors VII), 1995, pp. 212-223.

L. Küpper, H. M. Heise, L. N. Butvina; "Novel Developments in Mid-IR Fiber-Optic Spectroscopy For Analytical Applications"; Journal of Molecular Structure vol. 563-564, Elsevier, 2001, pp. 173-181.

METHOD AND APPARATUS FOR A MID-INFRARED (MIR) SYSTEM FOR REAL TIME DETECTION OF PETROLEUM IN COLLOIDAL SUSPENSIONS OF SEDIMENTS AND DRILLING MUDS DURING DRILLING OPERATIONS, LOGGING AND PRODUCTION OPERATIONS

This application claims the benefit of provisional U.S. Application No. 61/429,637, filed Jan. 4, 2001, the contents of which are incorporated herein by reference.

FIELD OF THE INVENTION

The field of the present invention relates generally to detection systems for oil drilling, logging and production operations, and more particularly to systems for analyzing aqueous colloidal suspensions produced during drilling, logging and production operations to detect the presence of petroleum.

BACKGROUND OF THE INVENTION

The detection of hydrocarbons while drilling is currently limited to the analysis of $C_1$-$C_6$ hydrocarbons entrained in the drilling mud. This is typically conducted by desorption of returned mud followed by a gas chromatographic analysis. The service is offered by many well logging companies. Conventional systems combine a rigorous sampling system coupled to a mass spectrometer, allowing precise fluid logging and analysis in real time.

Several service companies offer some form of downhole sensing for hydrocarbons. Most are based on resistivity measuring the difference between oil and water. Nuclear Magnetic Resonance (NMR) well logging is known in the prior art, and is used to detect and differentiate flowable oil from solid bitumens.

Several service companies offer spectrographic hydrocarbon detection systems. Typically, for such systems, a tool is lowered by wireline and uses a spectrometric sensor to determine if fluid flowing from a specific interval is liquid, gas, oil or water. The array of detectors include near IR, or visible light. These sensors are mostly designed to determine if the fluid flowing into a sample chamber is formation oil and represents a valid sample to bring to the surface for testing.

SUMMARY OF THE INVENTION

An object of the invention is to provide an improved system for detecting the presence of petroleum in aqueous colloidal suspensions proximate to a drill bit during drilling operations.

Another object of the invention is to provide an improved rapid response system using mid-infrared light emitters, waveguide and detectors for continuously providing an analysis of the level of petroleum produced proximate a drill bit during actual downhole drilling operations.

With these and other objects of the invention in mind, the present system in one embodiment of the invention includes means for producing a mid-infrared (MIR) light signal, waveguide means for receiving the light signal to generate an evanescent wave that is transmitted into drilling fluids being returned from the drilling bit to the drilling platform, light receiving means for receiving the evanescent wave after it has interacted with the returning drilling fluids passing over the waveguide, detector means for receiving the optical signal from the receiving means, means for processing the same into the mid-infrared spectra received from the waveguide, and means for transmitting or carrying the mid-infrared spectra to the drilling platform for continuously providing an indication of the presence or absence of petroleum, or other hydrocarbons, as drilling proceeds. The aforesaid elements are secured within a housing that is lowered into the drill pipe assembly at a position proximate to and above the location of the drill bit at any given time.

In another embodiment of the invention, memory means are included in the housing for continuously receiving and storing spectra produced by the detector means to insure later retrieval of the spectra being produced in the event that the spectra signals being transmitted to the drilling rig are interrupted, or in the event that such continuous output signal monitoring at the drilling rig is not utilized during particular periods of time.

In another embodiment of the invention, the aforesaid MIR evanescent wave detection system is duplicated within the housing, whereby the second MIR evanescent wave system is employed to retrieve MIR spectra from drilling fluids being pumped to the drill bit in order to provide a reference signal that is subtracted from the spectra signals being received from the associated first MIR evanescent wave detection system in contact with returning drilling mud containing cuttings and entrained hydrocarbons (if any) produced by the drilling operation, in order to eliminate or substantially reduce common mode signals therebetween, thereby enhancing the spectra being received from the returned drilling fluid.

In yet another embodiment of the invention, a plurality of juxtaposed waveguides are included for contacting the returned drilling fluid, whereby means are provided for selecting any one of the plurality of waveguides for use in a given period of time, thereby permitting switching from a waveguide that has become defective to one that is operable, and also permitting the use of different polymer coatings on each of the waveguides for enhancing the evanescent signals being received and/or for selectively receiving spectra of a desired wavelength associated with a particular hydrocarbon of interest, such as benzene, or toluene, for example. The embodiments of the invention utilizing a plurality of switchable waveguide means for each of the evanescent wave sensing systems, enhances the long term reliability of the system, and reduces downtime for repair of the system.

In yet another embodiment of the invention, the aforesaid MIR evanescent wave detection system is placed within a standard well logging tool stream and is used to detect hydrocarbons while logging.

BRIEF DESCRIPTION OF THE DRAWINGS

Various embodiments of the present invention are described in association with the drawings, in which like items are identified by the same reference designation, wherein.

DETAILED DESCRIPTION OF THE INVENTION

Figure 1:
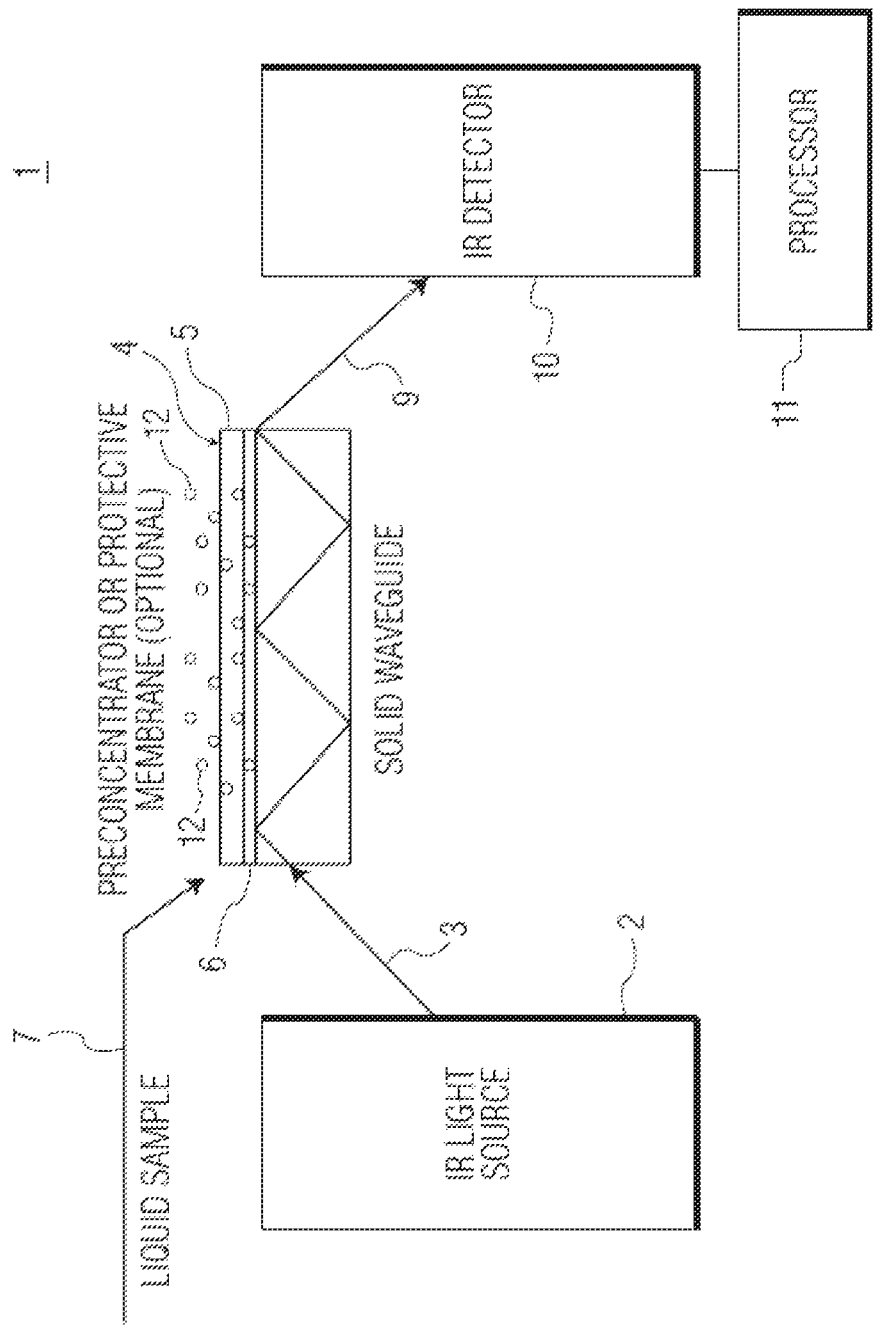
FIG. 1 shows a block schematic diagram of a conceptual system of the prior art for detecting the presence of analyte in fluids through use of MIR radiation, the sensing of evanescent wave or field sensing via electromagnetic radiation leaked into the liquid sample impinging upon the waveguide.

The present inventors recognize that there is a pressing need to improve systems for determining the presence of trace or minor quantities of oil in aqueous systems or water in oil systems throughout petroleum upstream and downstream operations. Such systems require sampling and analysis to be taken under hazardous or extreme environmental conditions. For example, analysis down a well bore requires a robust analyzer system about 4-6" in diameter and several feet in length capable of operating at depths of up to ~20,000 feet, temperatures of in excess of ~200° C., and pressures of greater than ~20,000 psi, and in the presence of acidic gases ($CO_2$ and $H_2S$) and high salinity. Determination of the presence of and quantification of $CO_2$, $C_1$-$C_{4+}$ hydrocarbons, Gas/Oil Ratio, and aromatic hydrocarbons such as benzene, toluene, and xylenes in a downhole fluid, allows one to determine the in situ composition at depth, and thereby the depth of "payzones" of interest. Potential applications, both downhole and on site at the drill head or other areas associated with the drilling operation include: 1) Improved mud logging (e.g., fluid composition and bypassed and proximity to pay decisions while drilling), 2) Improved well logging (e.g., fluid composition, reservoir delineation, and optimization of fluid sampling), 3) Logging while drilling (e.g., self-guided drilling, high-resolution continuous logging, and real-time decisions while drilling), 4) Development/Production (e.g., zone allocation and smart-well/reservoir performance, and 5) Environmental/Safety (e.g., spill-source identification, tank storage/pipeline leakage, site characterization, and long-term monitoring of remediation).

Present mid-infrared analyzer systems are generally composed of a source, wavelength dispersing component (prism, grating, interferometer, etc.), detector, and a sampling component to hold the fluid being analyzed. Analyzer systems using a mid-infrared waveguide analyzer allow one to eliminate traditional transmission type cells as the sampling component for the fluid. The waveguide analyzer element need only be in contact with the fluid to be analyzed, thereby eliminating variable pathlength considerations associated with transmission type cells and decreasing the overall size of the analyzer. In addition, waveguide-based analyzers are less susceptible to turbidity and opaqueness of the sample. Finally, waveguide analyzer elements enable additional surface modification (including but not limited to polymer membranes, sol-gel membranes, diamond-like carbon coatings, etc.) of the transducer for further enhancing selectivity, sensitivity, and robustness of the waveguide element for detection in corrosive environments.

Furthermore, using a waveguide analyzer in the mid-infrared region allows one to take advantage of the rich spectral "fingerprint" information available in this region for compositional analysis. Such rich spectral information is not available in the ultra-violet, visible or near infra-red spectral regions.

Quantum Cascade Lasers (QCLs), presently available at single wavelengths and tunable over a range of ±5% of the center wavelength, or used as an array of QCLs covering a broader spectral window, allow one to analyze either narrow or wide regions of the mid-infrared region of specific interest. Such an analyzer usually uses a transmission type cell as the fluid sampling component, but allows reduction in size of the source component of a mid-infrared analyzer system, thereby reducing analyzer size.

Typical downhole fluids are composed of a water based drilling mud (WBDM) or synthetic oil based drilling mud (OBDM). Hydrocarbon spectral signatures have been observed in WBDMs containing low levels of hydrocarbon. Low levels of hydrocarbons in OBDMs are more difficult to analyze because the low level hydrocarbon spectral signatures overlap the intense oil signatures present in the OBDM. Use of surface-modified (including but not limited to polymer membranes, sol-gel membranes, diamond-like carbon coatings, etc.) waveguide analyzers address this shortcoming by using the selective recognition and/or enrichment properties of the surface modification to enhance the concentration of the analyte of interest such as but not limited to aromatic hydrocarbons present in the fluid to be analyzed (benzene, toluene, and xylenes) near the surface of the waveguide thereby enhancing sensitivity and selectivity.

The techniques described above also have applications for the detection of water-in-oil mixtures. Mid-IR detection using uncoated waveguides has proven successful in distinguishing <0.1% water-in-oil mixtures. Trace amounts of water may be dissolved, or more likely, dispersed in crude oil as formations are tested both downhole, subsea, and on the surface, and as oil is produced and transported.

The invention provides systems for obtaining mid-IR (MIR) spectra suitable for determining the abundance and characteristics of crude oil and/or water under adverse, hazardous, or extreme environments where oil is present as a trace component in an aqueous system or water is a trace component in a hydrocarbon system. The detection of trace quantities of oil in oceanic, rivers, and lake waters or in near-surface (~<10 m) unconsolidated sediments will aid exploration in discovering the location and/or intensity of natural oil seeps. The present MIR detector systems can be used in remotely operated vehicles (ROV's), towed analyzers, or core samplers. Assuming that the present systems are rugged enough to survive on the drill string near the drill bit, direct detection of hydrocarbons in the drilling mud can be made to directly assist the drilling operation. Drill strings have been developed that allow high-speed, real-time data transmission while drilling. Coupling the present MIR sensing technology of various embodiments of the invention with known communication systems will allow signal processing on the surface, thereby permitting the information obtained to be used to make real time drilling decisions. Alternatively, data need not be transmitted back to the surface, but can be used to direct the direction of an autonomous drill bit, to allow "smart" drilling through long passages of horizontal production zones.

Hydrocarbon detection and characterization while well logging is envisioned as the most likely first application of the invention. Various known fluid analyzers are used by service companies mainly to determine if a suitable sample (e.g., oil rather than mud, gas or water) has entered a chamber. These fluids are then returned to the surface for analysis. The ability to not only detect but characterize a fluid's composition in-situ would lessen the need for costly sample recovery and provide a more detailed picture of the fluid dynamics within a reservoir (e.g., compositional gradients, current and paleo-oil/water and gas/water contacts) allowing improvements in field development and production.

The invention is envisioned in one embodiment to provide a system to be lowered on a wireline that provides both power and data communication. As the tool is lowered, selectively coated waveguides are placed against the formation to be tested and mid-IR spectra is obtained from fluid flowing from the zone of interest. Fluid composition is then inferred using chemometric processing of the mid-IR signal. Coatings specific for light aromatic hydrocarbons and/or $C_1$-$C_4$ organic acids can be used for indicators of proximity to pay and detect the presence of hydrocarbon in water legs associated with reservoirs not penetrated by the well.

Various embodiments of the invention can be used on the surface to analyze circulated mud for the presence of HC's in conjunction with mud gas detection systems already in wide use, if desired. The advantage of using a mid-IR sensing system of the present invention to detect higher hydrocarbons over more conventional methods (e.g., GC or GCMS) is that it requires little or no sample preparation, can be run by a technician with minimum training, and is rugged enough to survive the well site environment with little or no maintenance.

Alternatively, in another embodiment as described below, the tool or detection device is embedded in the drill pipe assembly as close to the drill bit as vibrational constraints will allow. It can be powered from the surface, and send spectra data to the surface in real time as drilling proceeds, and/or it can be battery powered and include a memory chip to store captured spectra data for later use. In this manner as described below for various embodiments of the invention, fluid composition can be monitored during production over tightly spaced zones. This provides an enabling technology for "smart field" production where production is automatically controlled for maximum economic yield.

The proper storage and disposal of oil-contaminated mud, water, and equipment can be monitored at the well site with strategically placed MIR-sensors of the present invention. These sensors can be employed to monitor the hydrocarbon content within and around waste pits to assure that contamination remains contained and for monitoring subsequent remediation of the area once drilling is complete. Similarly, the ability for rapid and widespread monitoring of hydrocarbon contamination in waste water will enhance refinery operations. Also, the detection of oil, gas, and water via the present invention tools or devices installed in pipelines, tankers, and other modes of transportation can be used to assess the potential for corrosive damage and monitor fluid quality, by detecting acid gases such as $CO_2$, and $H_2S$.

Several refinery processes will benefit by use of rugged sensors of various embodiments of the invention to detect trace hydrocarbons. For example, acid gases are scrubbed by flowing through amine solutions. The presence of trace amounts of condensate hydrocarbons can form emulsions. These emulsions are controlled with chemical additives, but the amine solution must eventually be replaced. Monitoring for trace condensate HC's will permit more efficient operation by monitoring the efficiency of the de-emulsifying chemicals.

Measurement via the present inventive devices of the water content in petroleum fluids, either during drilling or from evaluation tools allows for reliable determination of the water saturation, will permit accurate evaluation of the nature and extent of the transition zone, and determination of the oil-water contact. Currently, these are typically determined using resistivity measurements (difference in conductivity between saline water and petroleum); however, such measurements are of marginal value in reservoirs containing freshwater (e.g., lacustrine systems).

Sensing systems of the present invention are operable to detect changes in the water-content during production from sub-sea, offshore, and onshore production streams, thereby allowing for rapid response to changes in the oil-water cut of produced and commingled fluids. This information can be used to optimize formation, well, or combined field production to meet specific oil quality specifications. Also, accurate determination of the water content in oil is needed to assure that phase separation processes were effective such that the produced oil meets transportation specifications, and remains at specification during transport, can be provided through use of the present invention.

With reference to FIG. 1, a simplistic block schematic diagram is shown of a prior mid-infrared (MIR) optical sensing system that is operable for detecting and discriminating multiple analytes, as will be described in further detail below. As shown, the system 1 includes an infrared (IR) light source 2 capable of emitting light rays 3 in the MIR wavelength range from about 2.5 µm (micrometers) to 20 µm. The MIR light source 2 can be provided by any one of a number of light source devices, including a tunable diode laser (TDL), a quantum cascade laser (QCL), a tunable quantum cascade laser (TQCL), or a Fourier Transform infrared spectrometer (FTIR), for example, which example is not meant to be limiting. The light source 2 is used to transmit an MIR light ray into a waveguide 4. The waveguide 4, as shown, is a solid waveguide or thin film waveguide, but can otherwise be provided by an optical fiber waveguide, or a hollow waveguide. However, the inventors have determined that the waveguide 4 is more robust if provided by a solid waveguide, rather than by an optical fiber waveguide, or hollow waveguide. Suitable thin film waveguides are shown in U.S. Patent Application Publication No. US 2009/020642 A1, published on Aug. 20, 2009, under the title "Film Thin Waveguides, Methods of Fabrication Thereof, And Detection Systems," the teaching of which are incorporated herein to the extent they do not conflict herewith. Regardless, the outer surface of the waveguide 4 may be coated with a protective membrane 5 and/or with a hydrophobic polymer layer 6 that provides for an enrichment membrane for optimizing the detection of analytes in water, for example. As will be discussed in further detail below, when an MIR lightwave is passed into the waveguide 4, the waveguide 4 causes an evanescent field to be developed that is passed into the liquid sample 7 covering the waveguide 4, whereby molecules 12 of the liquid 7 interact with the evanescent wave, producing an evanescent wave modulated signal that is carried from the waveguide 4 via a light ray 9 to an IR detector 10. The IR detector 10 converts the received optical signal into an electrical signal, and feeds the same to a processor 11 that typically employs analog and digital processing of the received signal. In effect, the processor 11 is utilizing chemometrics for extracting information via data-driven means. In this example, the information is associated with the spectra of the molecules of the analyte excited by the evanescent field. Note that although a solid waveguide 4 is shown, it is not meant to be limiting, and although less preferred, the waveguide 4 can be provided by an optical fiber, or a hollow waveguide (for gas detection), as previously mentioned.

Broadly tunable laser light sources (such as, e.g., external cavity coupled tunable QCLs) or QCL arrays can preferably provide light source 2, to enable tailoring the sensor device or system 1 performance anywhere in between broadband and narrowband device concepts. Most commonly, IR sensors are combined with Fourier transform infrared (FT-IR) spectrometers or grating spectrometers inherently providing the capability of multi-component analysis and a high degree of flexibility. Miniaturized sensors for target analysis utilize tunable lead salt laser diodes or, more recently, quantum cascade lasers. Also, optical parametric oscillators (OPO) gain importance as mid-IR light source as physical dimensions of OPOs decrease. While light emitting diodes (LEDs) in the mid-infrared range are commercially available, their applicability is limited due to low radioactive energy output. At high concentration levels, the combination of black body radiators with wavelength selecting bandpass filters certainly represents a cost efficient solution.

Fiber optic sensing schemes are divided into two main groups: (i) direct sensors directly detecting changes of optical properties or spectral characteristics of the sample, and (ii) indirect sensors or indicator-based sensors utilizing various types of chemical recognition processes translating chemical signals generated at the interface with the sample into changes of analyte specific optical signatures. In the latter, characteristic spectral IR features of analytes are investigated after membrane extraction or membrane enrichment within the probed analytical volume. Ideally, the sensing membrane is directly coated onto the transducer surface. Frequently, such systems are classified as physico-chemical sensors. Most mid-infrared sensing schemes are based on the fundamental principle of internal reflection spectroscopy (IRS) or more specifically attenuated total reflection (ATR).

Total internal reflection of electromagnetic radiation occurs, when light rays 3 at an angle of incidence greater than a critical angle $\theta_c$ (with $\theta_c$=arcsin $n_2/n_1$) is reflected at the interface between the optically denser waveguide 4 and the adjacent optical thinner medium 6, e.g., a polymer enrichment membrane 6 coated onto the waveguide's surface (see FIG. 1). The result of the total internal reflection process is that part of the electromagnetic radiation that is propagating along the waveguide surface leaks into the contiguous environment. Such externally guided radiation is called an evanescent wave or evanescent field, as previously mentioned. The evanescent wave penetrates with exponentially decaying field amplitude into the adjacent medium and interacts with molecular species 12 present within the probed analytical volume.

For a waveguide 4 (refractive index $n_1$) and an adjacent sample medium or an enrichment membrane 6 coated on top of the waveguide (refractive index $n_2$) with $n_1 > n_2$, at a given wavelength $\lambda$ the penetration depth of the evanescent field $d_p$ can nominally be calculated as shown below in Equation 1:

$$d_p = \frac{\lambda}{2\pi\sqrt{n_1^2\sin^2\theta - n_2^2}}. \quad (1)$$

For aqueous phase measurements the thickness of the enrichment membrane 6 is selected to be larger than the maximum nominal penetration depth of the evanescent field in the spectral region of interest. Waveguide-protective coatings 5 such as, e.g., diamond-like coating (DLC) may be much thinner than the penetration depth, as direct sensing is applied. Any combination of thin-film protective coatings 5 overcoating enrichment membranes 6 is, of course, possible. Using hydrophobic polymers for the membranes 6 for providing analyte enrichment will minimize the presence of interfering water within $d_p$ for IR chemical sensors. The interaction of the evanescent field with enriched molecular or ionic species 12 provides IR spectra similar to conventional absorption measurements recorded in a transmission arrangement. Advantageously, the evanescent wave propagates at the waveguide/membrane interface. Minimal disturbances from adverse physical properties of the sample matrix, such as turbidity, have been confirmed.

ATR spectroscopy in the mid-infrared spectral range has become a well-established and widely used technique in analytical chemistry utilizing conventional macroscopic ATR waveguide elements made from materials such as zinc selenide (ZnSe), zinc sulfide (ZnS), various thallium bromides (KRS-5, etc.), germanium (Ge), or silicon (Si), and shaped as prism, trapezoid, rod or hemisphere. However, only the introduction of mid-infrared transparent fiber optics enabled converting this laboratory technique into what is now called fiber optic evanescent wave sensing (FEWS) technology.

Infrared optical fibers are defined as waveguides transmitting radiation at wavelengths >2 μm. According to the fundamental material properties they are divided into four main categories: glass fibers (e.g., chalcogenides, fluorides), (poly) crystalline fibers (e.g., silver halides, sapphire), hollow waveguides (e.g., hollow silica or sapphire tubes), and solid waveguides (e.g., thin film planar GaAs/AlGaAs).

Non-silica-based IR transparent fibers first appeared in the 1960s and were made from arsenic trisulfide. It was not until the early 1970s that single crystal fibers were reported with a wide variety of new IR transparent waveguides to follow soon thereafter based on demand driven by short-haul military applications and surgical $CO_2$ laser radiation delivery.

Despite their advantageous chemical and mechanical properties only a few sensing applications of sapphire fibers are reported including the measurement of gaseous hydrocarbons at high temperatures and cycle-resolved vehicle engine emission monitoring.

Fluoride fibers are characterized by low attenuation losses. However, their MIR transmission window is limited and they are susceptible to moisture. Applications have been demonstrated, e.g., for the investigation of propane diffusing into a Teflon cladding.

Chalcogenide glasses are considered the technically most advanced IR fiber optic waveguides and have been used, e.g., for remote hydrocarbon gas sensing and for the determination of organic solutes in water.

Tellurium halide fibers are highly resistant against corrosion and degradation with applications reported, e.g., for the spectroscopic determination of alcohol in water.

Silver halide fibers are among the most promising materials for the development of fiber optic IR sensor providing access to the whole MIR spectral range of interest (2.5-25 μm). Due to the versatility of these fibers a wide variety of sensing applications for the detection of organic compounds have been reported.

Using structural tubes made from dielectrics, metals or metal coated materials provide hollow waveguide structures considered as optical fiber with an air core. IR radiation is guided by reflection at the inside walls. Hollow waveguides simultaneously acting as capillary flow cell enable gas sensing applications for a multitude of relevant compounds.

Finally, thin-film planar GaAs/AlGaAs waveguides 4 have recently revolutionized IR sensing by enabling the full integration of structured MIR transparent waveguides onto the wafer scale. Thereby, the—hybrid or even monolithic—integration of entire IR sensing devices combining QCLs, waveguide (transducer) and detector is facilitated for the first time.

Various embodiments of the present invention will now be described in detail below.

Hydrophobic polymer layers 6 (including but not limited to Teflon AF (1601, 2400), poly(dimethylsiloxane) (PDMS), poly(isobutylene) (PIB), poly(ethylene-co-propylene) (E/Pco), poly(styrene-butadiene) (PSB), low density polyethylene (LDPE), polybutadiene cis/trans (PBCT), poly(acrylonitrile-co-butadiene) (PAB), poly(acrylate) (PA), poly (dimethylsiloxane)/poly(divinylbenzene) (PDMS/DVBS), and poly(ethylene glycol)/poly(divinylbenzene) (Carbowax/DVB). Organically modified sol-gels (ORMOSILs, etc.) are coated onto the actively transducing waveguide 4 surface following the general concept of solid phase microextraction (SPME). Hence, water is widely excluded from the analytical volume probed by the evanescent field. As an example, water/polymer partition coefficients of volatile chlorinated hydrocarbons may range from 100 to 10,000. Appropriate membrane selection is based on screening the partition coefficients of selected analytes between liquid phases or mud based samples and the respective polymer membranes.

Selection of appropriate enrichment membranes is of use for optimizing the limit of detection (LOD), while the coating thickness will mainly influence the sensor response time. As recently modeled, the sensor response time is substantially affected by the diffusion behavior of analyte molecules in the water column. Minimized time to reach equilibrium conditions is positively promoted by higher flow velocities and higher diffusivity, which can be accomplished by optimized flow cell design.

Protecting the waveguide 4 surface from corrosion in harsh environments is an aspect of the present invention. Diamond-like carbon (DLC) layers (50-200 nm thick) 5 serve as a robust IR-transparent thin-film protection at the waveguide 4 surface. These layers may of course be combined with an enrichment scheme, as discussed above.

Selection of appropriate detection schemes is among the parameters determining the achievable limit of detection. Broad-band semiconductor detectors, such as liquid $N_2$ cooled mercury-cadmium-telluride (MCT) systems, are most commonly used for high-sensitivity applications. Various detector materials with broad- or narrowband response are available throughout the entire mid-infrared spectral range. Field deployable IR sensors usually rely on thermoelectrically cooled MCTs or room-temperature operated deuterated tryglycine sulfate (DTGS) detectors. Semiconductor detector elements may be packaged within miniaturized closed-cycle Stirling coolers providing operation temperatures as low as 77 K in a detector package of approx. 10 $cm^3$. Less costly detector solutions for higher concentration ranges are based on pyroelectric materials or thermopiles. Microfabricated wavelength selective detection devices based on quantum well infrared photoconductive (QWIP) detectors or microbolometers are of increasing importance in combination with monochromatic light sources.

Figure 2:
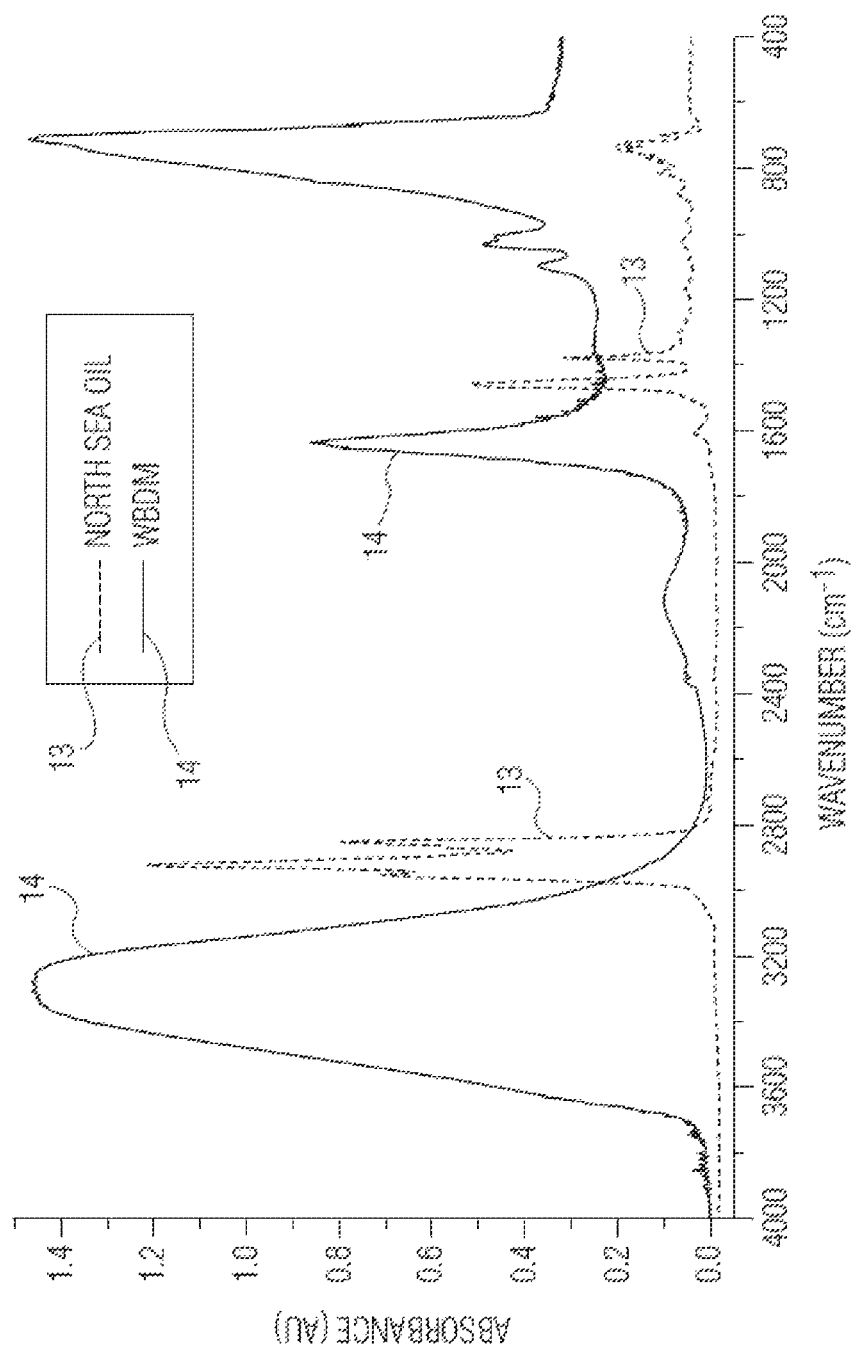
FIG. 2 shows MIR spectra plots obtained from pure North Sea oil, and from water-based drilling mud (WBDM) through use of a waveguide IR-spectrometer, for an embodiment of the invention.

The ability of a mid-IR spectrometer to detect trace amounts of oil in a synthetic water-based drilling mud was tested by the inventors in a series of experiments using uncoated and coated waveguides. In FIG. 2, the mid-infrared (MIR) spectra of pure North Sea Oil (NSO) 13, and water-based drilling mud (WBDM) 14 are shown.

The water-based drilling mud (WBDM) 14 exhibits a large broad absorbance feature from ~3800 to 2800 $cm^{-1}$ due to water, while the North Sea oil (NSO) 13 is characterized by a sharper absorbance feature at 3000-2850 $cm^{-1}$ due to the stretch of C—H bonds. Other absorbance features at ~1470 $cm^{-1}$ and at ~1380 are due to the C—H scissoring and C—H methyl rocking.

Figure 3:
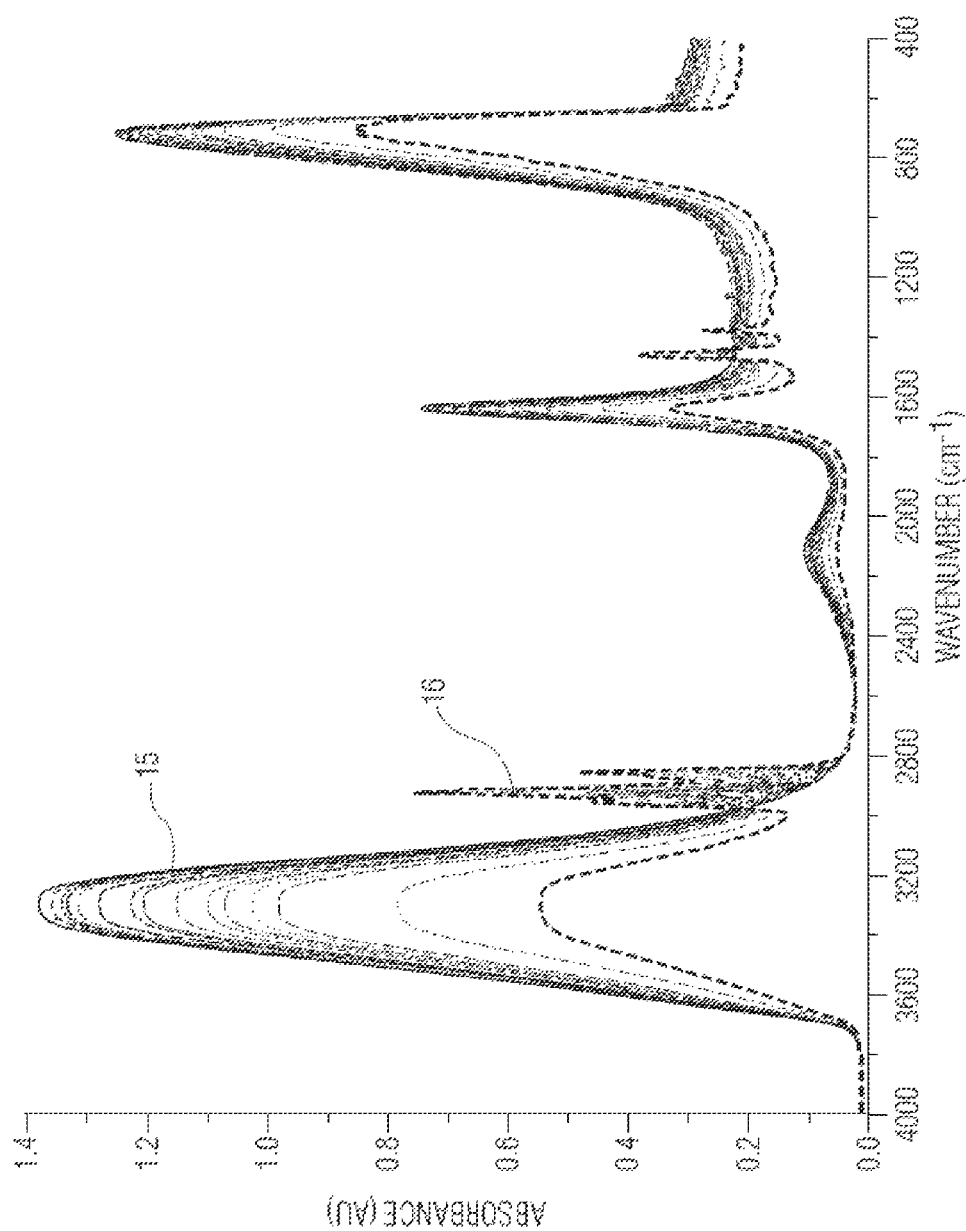
FIG. 3 shows a MIR spectra plots obtained from the North Sea oil mixed with pure water via laboratory experiments using a waveguide IR-spectrometer, for an embodiment of the invention.

Mixing varying trace amounts of oil in pure water result in the hydrocarbon signatures superimposing on the water spectra, as shown in FIG. 3. The ~3000-2850 $cm^{-1}$ region proves to be most useful for detecting the North Sea oil signature 16 with the absorbance diagnostic of the amount of added oil. The level of detection is conservatively estimated to be ~0.005%. The NSO mixed with pure water exhibits a large broad absorbance feature 15 from about 3800 $cm^{-1}$ to 2800 $cm^{-1}$ due to water. Other absorbance features at about ~1470 $cm^{-1}$ and ~1380 $cm^{-1}$ are due to C—H scissoring and C—H methyl rocking. Similar test were conducted on oil in unconsolidated sediments (Gulf of Mexico). The level of detection is conservatively estimated to be ~0.04%.

For determining the level of oil detectable in synthetic water-based drilling mud (WBDM), a blind-test was conducted whereby four samples of varying oil concentration were prepared by other than the present inventors, and analyzed without their prior knowledge of the concentrations. These tests were conducted using uncoated zinc selenide waveguide. Of the four samples, all but WBDM-1 were above background and were reported with measurable oil. After completion of the test, the concentrations of the mixtures were revealed to be as shown below in Table 1:

TABLE 1

| WBDM Sample | % NSO (vol:vol) in WBDM |
|---|---|
| WBDM-4 | 4.656 |
| WBDM-2 | 0.863 |
| WBDM-3 | 0.105 |
| WBDM-1 | 0.012 |

Figure 5A:
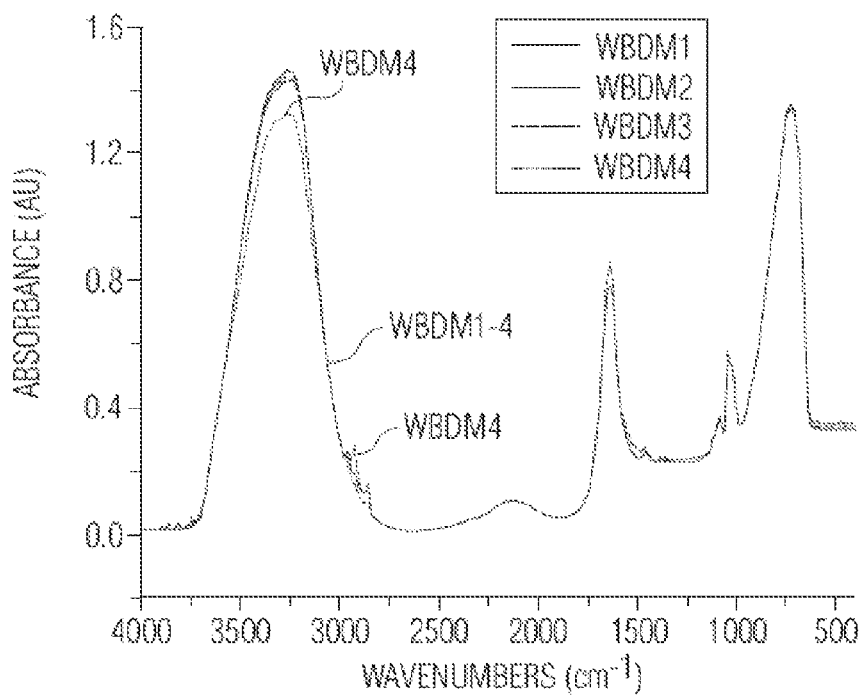
FIG. 5A shows spectra plots of North Sea oil (NSO) and in synthetic WBDM at varying concentrations of oil using an IR-spectrometer and an uncoated zinc selenide waveguide, for an embodiment of the invention.
Figure 5B:
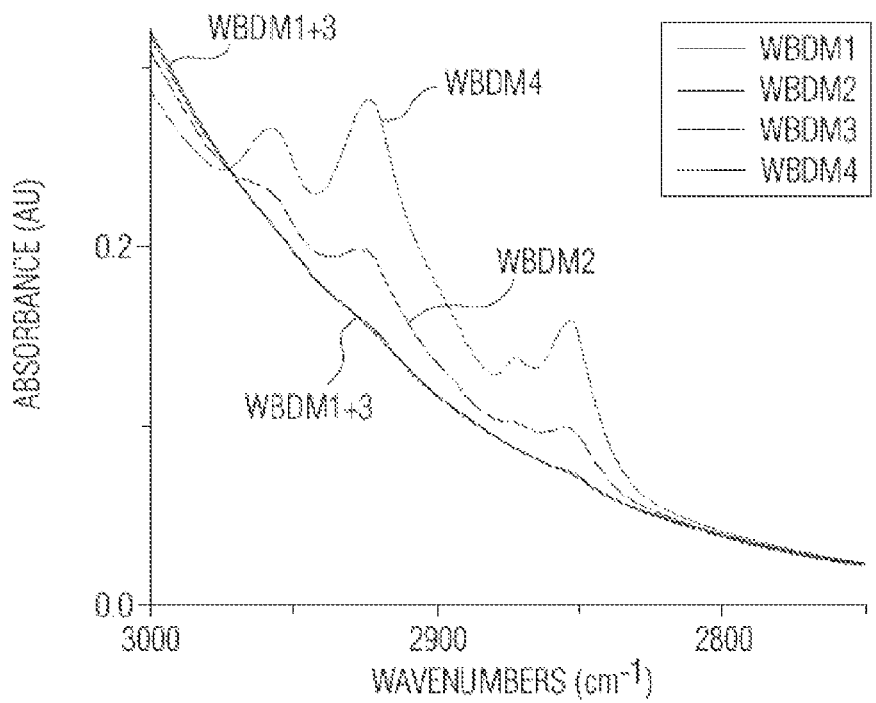
FIG. 5B shows an enlarged detailed view from FIG. 5A of spectra from 2,800 to 3,000 $cm^{-1}$, for an embodiment of the invention.
Figure 6A:
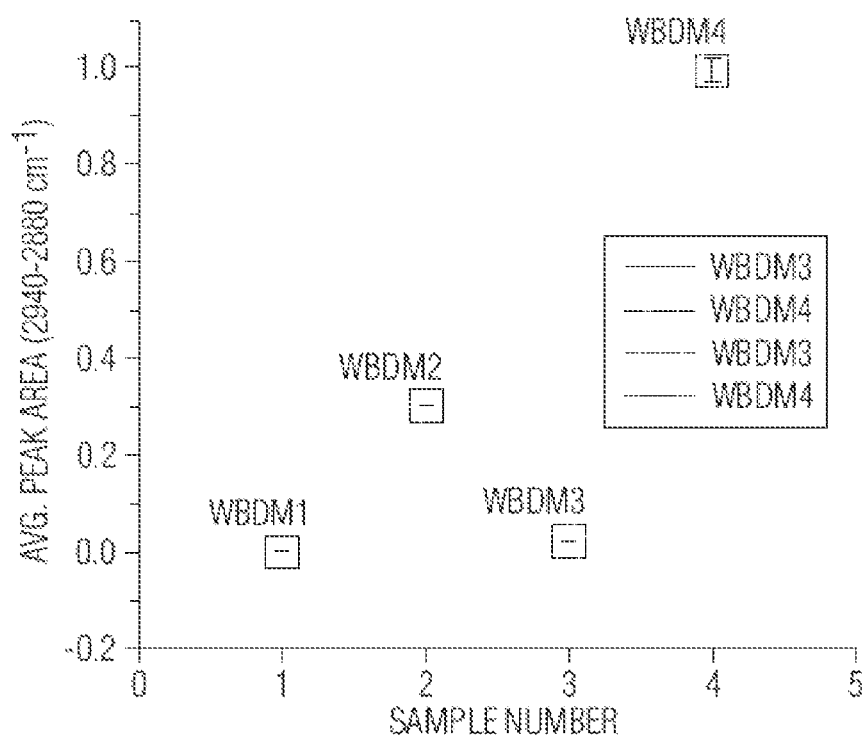
FIG. 6A shows the average peak area 2,800-3,000 $cm^{-1}$, background subtracted, for the four NSO-WBDM samples shown in FIGS. 5A and 5B, pursuant to the invention.
Figure 6B:
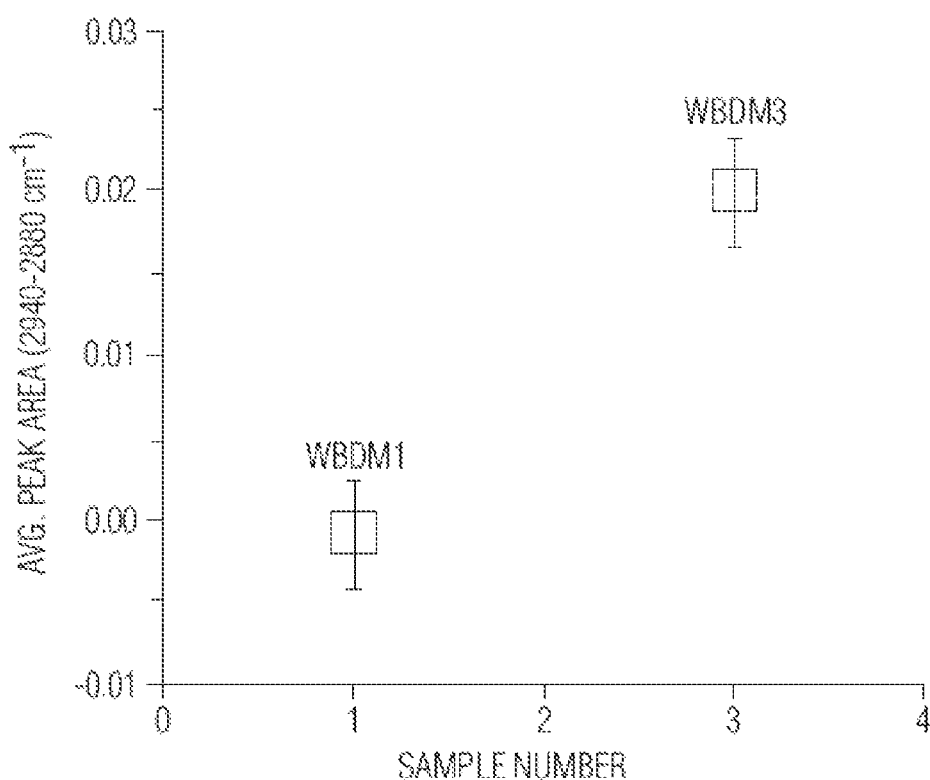
FIG. 6B shows an enlarged area of FIG. 6A.

Based on these values, a lower limit of detection of oil using an uncoated waveguide was ~0.1%. FIGS. 5A and 5B show the spectra obtained. FIGS. 6A and 6B show the Average Peak Area 2800 $cm^{-1}$ to 3000 $cm^{-1}$, background subtracted, for the four samples of NSO WBDM 1-4 of FIGS. 5A and 5B.

Figure 4A:
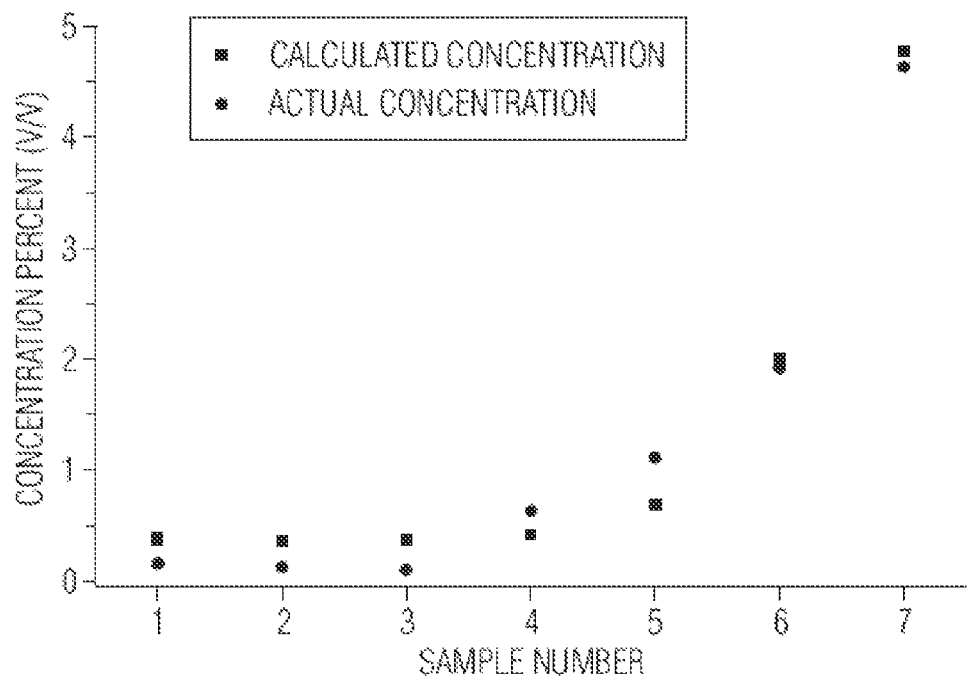
FIGS. 4A and 4B show graphs of Concentration Percent (V/V) vs. Sample Number, and a calibration plot establishing that oil-in-water concentrations greater than 1% can be measured with a high degree of accuracy, with lower concentrations being approximated with semi-quantitative results, for various embodiments of the invention.
Figure 4B:
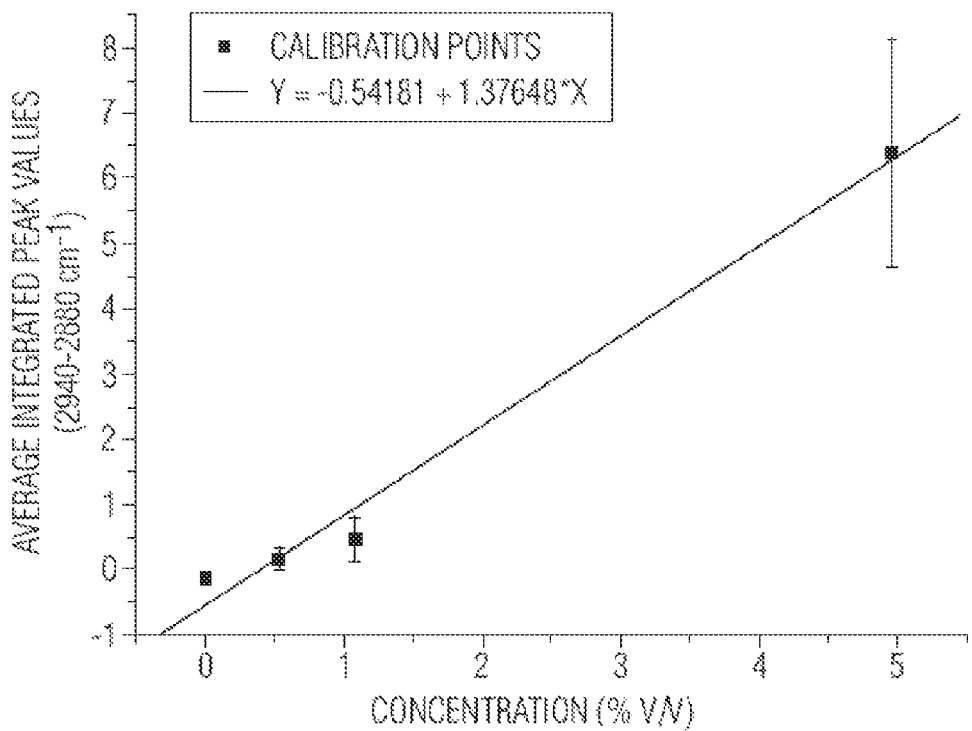

Additional tests, the results of which are shown in FIGS. 4A and 4B, show that a calibration curve can be established such that oil-in-water concentrations >1% can be measured with a high degree of accuracy while lower concentrations can be approximated with semi-quantitative result. Concentrations <0.5% are difficult to quantify due to oil agglomeration and phase separation.

Tests conducted by the inventors with a zinc selenide waveguide coated with an ethylene/propylene co-polymer enrichment membrane demonstrated the capability of selective detection of light aromatic species (benzene, toluene, and xylenes, BTX) in oil-water mixtures. The polymer coating enriches the material exposed to mid-IR detection by selectively absorbing BTX dissolved in either water or from water-based drilling muds. In these experiments, 50 ppm tetrachloroethylene (TeCE) was spiked into the North Sea Oil (NSO) to provide an estimate of relative abundance.

Figure 7:
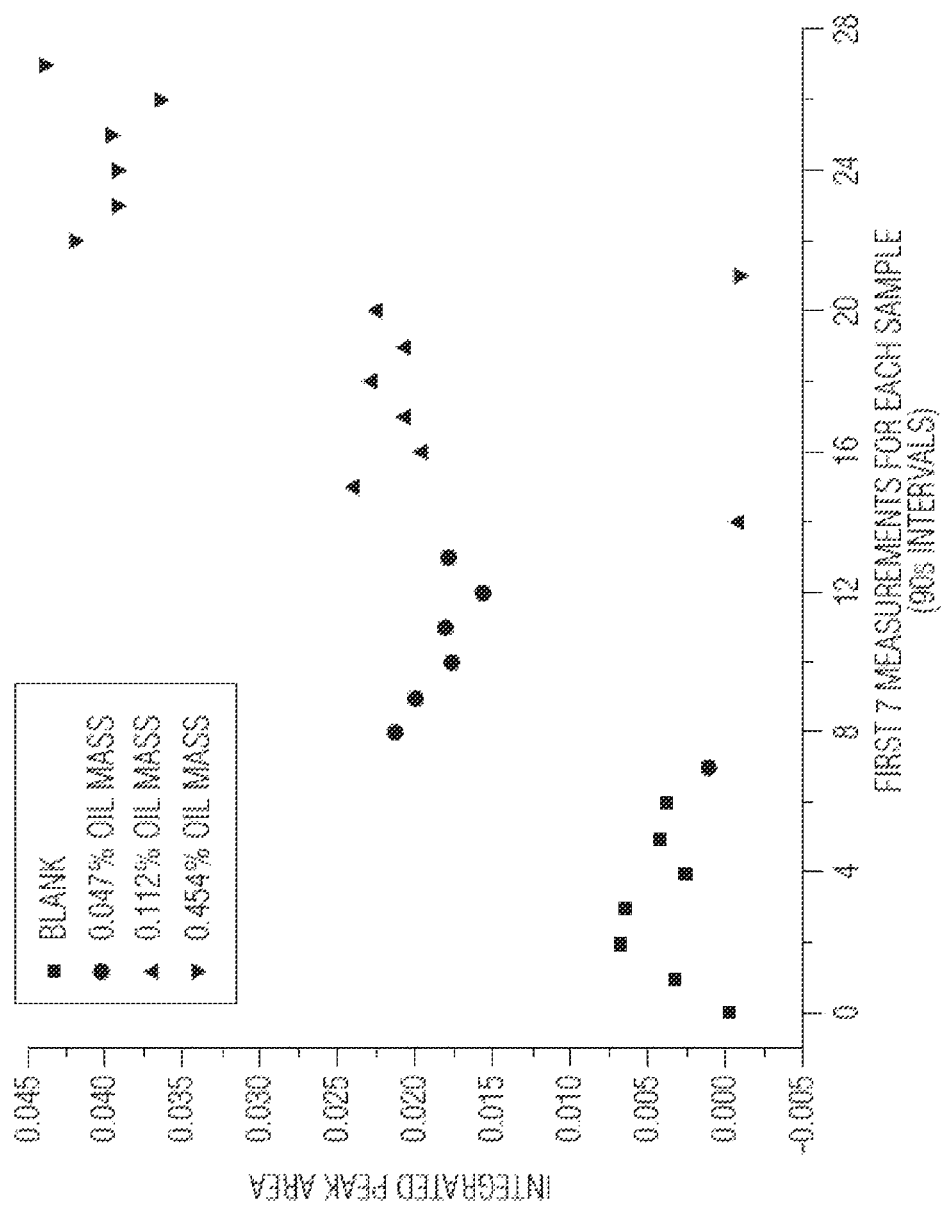
FIG. 7 shows plots of the peak area over 2,800-3,000 $cm^{-1}$ for synthetic mixtures of North Sea oil in the Gulf of Mexico sediments, for an embodiment of the invention.

FIG. 7 plots the peak area over 2800-3000 $cm^{-1}$ for synthetic mixtures of North Sea oil in Gulf of Mexico recent sediments. The level of detection and reliability of quantification are similar to that seen for oil-WBDM mixtures.

Figure 8:
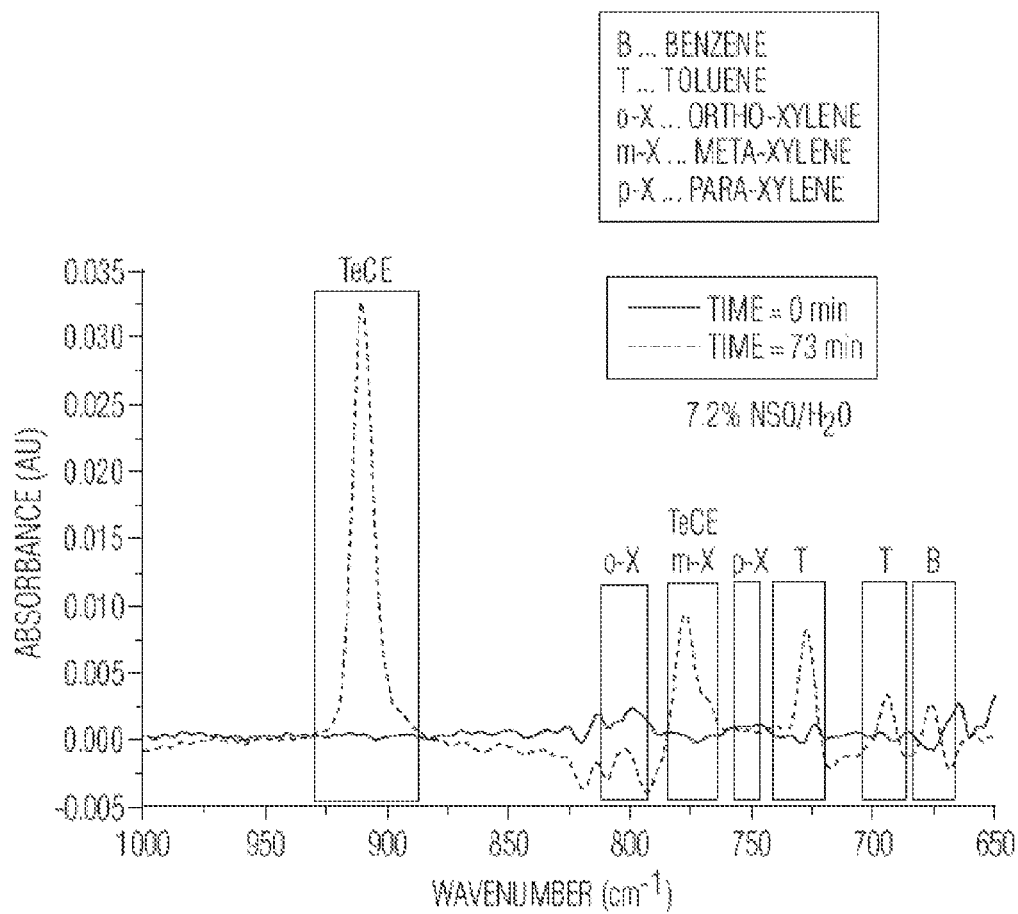
FIG. 8 shows MIR spectra obtained from laboratory tests conducted with a zinc selenide waveguide coated with an ethylene/propylene co-polymer enrichment membrane for demonstrating the capability of selected detection of light aromatic species (benzene, toluene, and xylenes, otherwise known as BTX) in oil-water mixtures, for an embodiment of the invention.

FIG. 8 shows results from a series of tests conducted with a zinc selenide waveguide coated with an ethylene/propylene co-polymer enrichment membrane demonstrated the capability of selective detection of light aromatic species (benzene, toluene, and xylenes, BTX) in oil-water mixtures. The polymer coating enriches the material exposed to mid-IR detection by selectively absorbing BTX dissolved in either water or from water-based drilling muds. In these experiments, 50 ppm tetrachloroethylene (TeCE) was spiked into the North Sea Oil (NSO) to provide an estimate of relative abundance. Accordingly, these tests demonstrated the enrichment of the BTX and the TeCE spike, and detection thereof by mid-FTIR (Fourier transform IR). From the response over time, the inventors determined that near equilibrium occurs after about thirty minutes. The inventors further recognized that since different coatings can be utilized that are respectively sensitive to different types of petroleum compounds, an array of detectors or waveguides each with different polymer coatings will permit detection of detailed compositional information.

Figure 9:
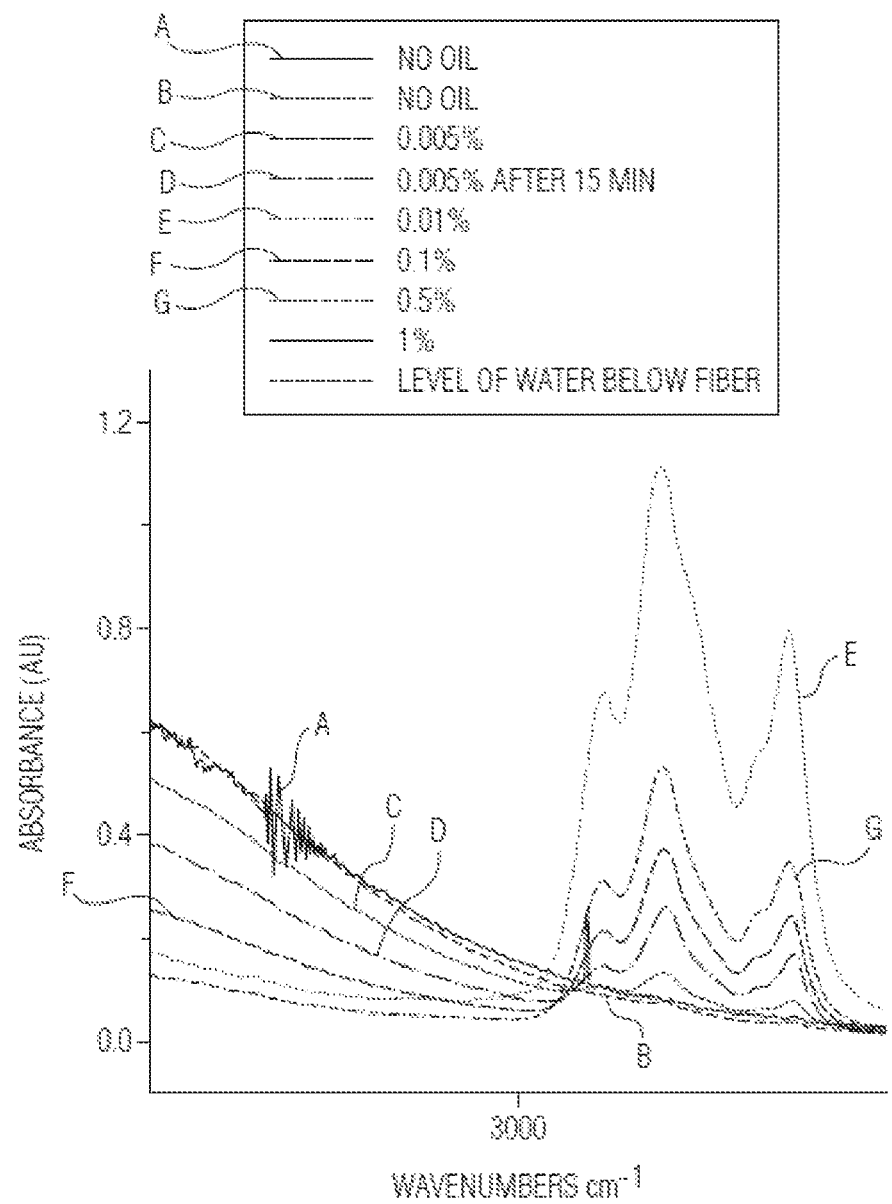
FIG. 9 shows MIR spectra obtained fro the detection of trace amounts of oil-in-water using an uncoated ZnSe waveguide.

FIG. 9 shows spectra obtained for the detection of trace amounts of oil-in-water using a uncoated ZnSe waveguide. All measurements used a resolution of 1 $cm^{-1}$. All samples were prepared by mixing oil and water using magnetic stirring bar/magnetic stirring plate for 45 min. One mL of the sample was then deposited on the deposited on ZnSe crystal and each sample was analyzed for 45 min (30 spectra were taken) with resolution 1 $cm^{-1}$. Based on these results the limit of detection was ~0.1% of water in oil. However, it was noted that the absorbance of OH peak increases with additional time due to separation of water and oil on ZnSe crystal. Nevertheless, these experiments show that technique can provide semi-quantitative measurement of trace amounts of oil-in-water.

As previously mentioned, the present invention is mainly for measuring trace or minor quantities of oil in aqueous colloidal suspensions of geologic sediments and/or drilling muds or trace or minor quantities of water in petroleum systems in real time as drilling proceeds. The invention consists of a mid-infrared spectrometer and the application of the mid-infrared spectrometer to colloidal systems. Referring again to FIG. 1, the basic invention includes an IR light source 2 for emitting mid-infrared radiation 3, an optical fiber (not shown) for carrying the MIR from the source 2 into a coated or non-coated waveguide 4, and another optical fiber (not shown) for carrying a modulated MIR light signal 9 from waveguide 4 to an IR detector 10.

The MIR light source 2 can be one of several conventional devices, but preferably is a quantum cascade laser (QCL) capable of emitting at one or more specific wavelengths. The emergence of broadly tunable laser light sources (such as, e.g., external cavity coupled tunable QCLs) or QCL arrays enable tailoring the sensor performance anywhere in between broadband and narrowband device concepts. In the best practice implementation of the invention, a quantum cascade laser or lasers are used as the source(s) emitting at a fixed or variable frequency.

The IR detector 10 can be provided by several conventional sensors (e.g., broad-band semiconductor detectors, pyroelectric materials or thermopiles, and so forth, as mentioned above) or, in the preferred embodiment, is a microfabricated wavelength selective detection device based on quantum well infrared photoconductive (QWIP) or microbolometers in combination with monochromatic light sources.

The present invention is directed to application of MIR-ATR spectroscopy for HC-detection in aqueous colloidal suspensions such as drilling muds coupled with the adaptation of novel technologies such as QCLs, thin-film waveguides, and quantum well infrared photoconductive detectors, for example. The present invention includes the use of this instrumentation to detect minor or trace amounts of petroleum within an aqueous colloidal suspension involving drilling mud, drill cuttings, and unconsolidated sediments. Through the previously discussed experiments, the inventors determined that using a waveguide analyzer in the mid-infrared region allows one to take advantage of the rich spectral "fingerprint" information available in this region for compositional analysis. Such rich spectral information is not available in the UV/Vis or NIR (near infrared) regions used in the systems of the prior art. The present invention provides for detection of generic hydrocarbons, or through the use of selective wavelengths and waveguide coatings, the detection of specific hydrocarbons, such as benzene and toluene.

Potential applications for the present invention, both downhole and on site at the drill head or other areas associated with the drilling operation include improved mud logging (fluid composition and bypassed and proximity to pay decisions while drilling); improved well logging (fluid composition, reservoir delineation, and optimization of fluid sampling); logging while drilling (self-guided drilling, high-resolution continuous logging, and real-time decisions while drilling); detection of oil-based drilling mud in connate water samples; development-production (zone allocation and smart-well/reservoir performance); and/or environmental/safety (spill-source identification, tank storage/pipeline leakage, site characterization, and long-term monitoring of remediation). Other potential applications involving detecting minor or trace amounts of petroleum in recent sediments can include: in situ detection of natural petroleum seepage in sediments; detection of natural petroleum seepage in sediments recovered as cores or grab samples and brought to the surface; in situ detection of petroleum and recovered sediments resulting from accidental release; and/or measurement of petroleum contamination in controlled effluent releases such as used drilling mud, sewage treatment, and ship bilges.

Trace amounts of water may be dissolved, or more likely dispersed, in crude oil as formations are tested both downhole, subsea, and on the surface, and as oil is produced and transported. Applications for detecting water-in-oil include (but are not limited to) measurement in drill stem test fluids to determine depth and extent of oil-water contact, reservoir transition zone, and water saturation; real-time monitoring of production fluid quality from either discrete formations, single-well, or commingled field operation; chemical-injections during well testing and treatment; top-side facilities such as fluid separators; oil quality measurements to meet pipeline and transport specifications; and monitoring of water washing and/or desalting operations.

Figure 10:
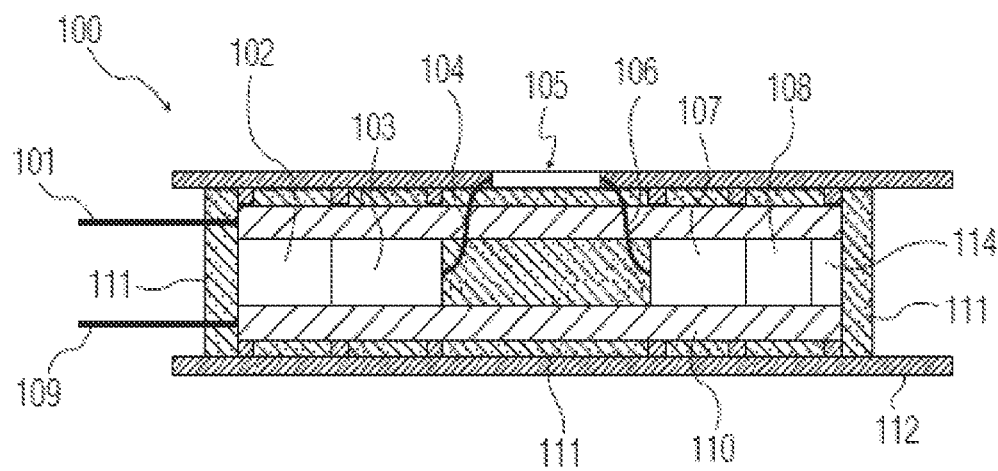
FIG. 10 shows a block schematic diagram of a portion of a wireline logging tool or device for a first embodiment of the invention.

With reference to FIG. 10, an embodiment of the invention for a device or sensor apparatus 100 for determining the amount of petroleum in drilling mud is for inclusion in a wire line logging tool assemblage, as described below for FIG. 12. Power is provided by the wire line or power cable 101 into a bus array 111, or by batteries (not shown). A source controller 102 regulates an MIR source 103 to assure emission of mid-infrared radiation at a constant output over a fixed range of frequency or at specific frequencies, in a pulsed or continuous mode, for example. The MIR light source 103 is preferably a quantum cascade laser (QCL) that is designed to emit MIR rays at variable or fixed wavelengths. Other more conventional sources may be used, but with lower or less exact emissions and/or higher power requirements, as previously mentioned.

The emitted radiation (MIR light ray) is conveyed via an optical fiber or cable 104 to a waveguide 105. The MIR source signal propagates through the waveguide 105 via a series of internal reflections. The result of the total internal reflection process is that part of the electromagnetic radiation that is propagating along the waveguide surface leaks into the contiguous environment. Such externally guided radiation is called the evanescent wave or evanescent field, as previously mentioned. The evanescent wave penetrates with exponentially decaying field amplitude into the adjacent medium and interacts with molecular species present within the probed analytical volume. This interaction causes the evanescent wave to be modulated. The outer surface of the waveguide 105 is in contact with the drilling mud and formation fluids that are swept over the waveguide, in this example. The waveguide can be coated with diamond-like substances 5 (see FIG. 1) for robustness and/or polymer coatings 6 (see FIG. 1) that are selective for specific types of hydrocarbons, e.g., benzene and toluene.

The evanescent wave modulated signal is conveyed via an optical fiber or cable 106 to a detector 107, which in the preferred embodiment is a quantum well infrared photoconductive detector. Other more conventional detectors may be used, but with lower sensitivity, less resolution, and/or higher power requirements. A detector controller 108 operates the detector 107, provides automatic gain control (AGC), processes the output signal from the detector 107, and sends a processed signal to the surface 409 via a signal wire line 109. Alternatively, the detector controller 108 may store the data or processed signal in a flash memory 114 for retrieval after the device or sensor apparatus 100 is removed from the associated wellbore. Alternatively, at the same time data is being stored in memory 114, it can also be transmitted to the surface via signal line 109. The MIR source 103, waveguide 105, detector 107 and associated electronic system for controllers 102 and 108 are mounted between an electrically conductive bus array 110 that provides both support and power/data communication between the controllers 102 and 108. The entire unit is sheathed within heat resistant insulators 111 (ceramic material, for example) and housed in a steel container 112 (corrosion-resistant high strength steel, for example) that may be included in or segmented with other well logging tools.

Figure 11:
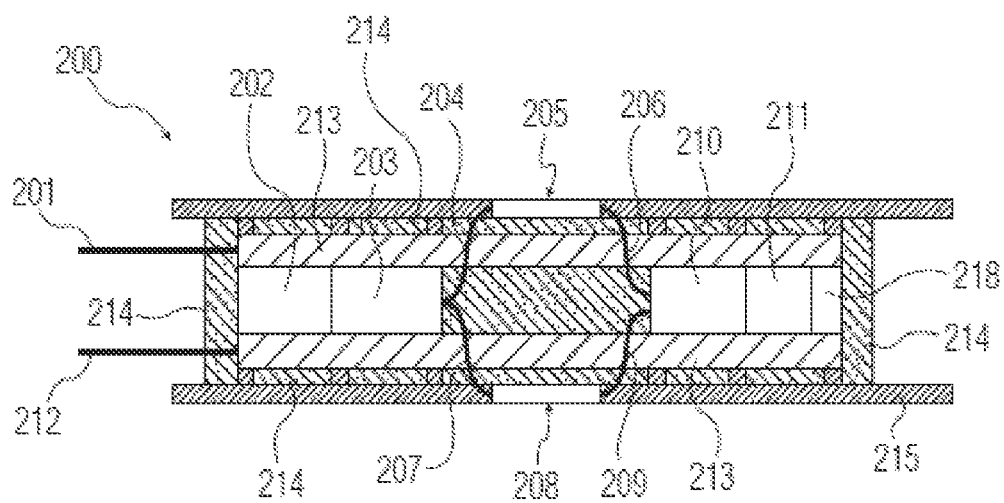
FIG. 11 shows a block schematic diagram of a wireline logging tool or device of a second embodiment of the invention.

In another embodiment of the invention, a tool or device or apparatus 200 for determining the amount of petroleum in drilling mud as part of a system to take measurements while drilling, is shown in FIG. 11. Power is provided by batteries (not shown) or from the surface via power line or cable 201 into a bus array 213 for distributing power. A source controller 202 regulates an MIR light source 203 to assure emission of mid-infrared radiation at a constant output over a fixed range of frequency or at specific frequencies. The MIR light source 203 is ideally a quantum cascade laser that is designed to emit at variable or fixed wavelengths. Other more conventional sources can be used, but with lower or less exact emissions and/or higher power requirements.

The emitted MIR light ray is conveyed via an optical fiber or cable 204 to a waveguide 205. The outer surface of the waveguide 205 is in contact with the drilling mud as it is pumped to the drill bit. The waveguide 205 can be coated with diamond-like substances 5 (reference FIG. 1) for robustness and/or polymer coatings 6 (reference FIG. 1), as previously described, that are selective for enhancing signal pickup and/or for specific types of hydrocarbons, e.g., benzene and toluene. The modulated signal produced is sent via an optical fiber or cable 206 to a detector 210. A second source signal is conveyed via an optical fiber or cable 207 to a second waveguide 208 that is coated in the same manner as waveguide 205. Waveguide 208 is in contact with the returning drilling mud that contains cuttings and entrained hydrocarbons liberated by the drilling. The signal from waveguide 208 is conveyed via an optical fiber or cable 209 to the detector 210. A detector controller 211 is programmed to operate the detector 210, and compares the signals from the introduced drilling mud and the returning drilling mud. The signals are processed by controller 211 to subtract the background spectrum or background signal (common mode) from the return signal, thereby improving the signal-to-noise ratio for the spectra of interest. Entrained or emulsified petroleum is detected by processing the difference signal. The processed signal from detector controller 211 is sent to the surface via signal line or cable 212 and/or to a data storage device, such as a flash memory 218, for retrieval after the sensing tool or device or apparatus 200 is removed from the wellbore (not shown). The MIR source 202, waveguides 205 and 208, detector 210, associated electronic circuits and networks for controllers 203 and 211 are mounted between bus 213 that provides both mechanical support and power/data communication between the controllers 203 and 211. The entire unit 200 is sheathed within heat resistant insulator material 214 that also provides shock protection, and further housed in a steel container 215 that is embedded within a drill pipe (see FIG. 13). The insulator material 214 can be ceramic or sapphire material, and the steel container 215 can be corrosion resistant stainless steel or titanium, for example.

Figure 12:
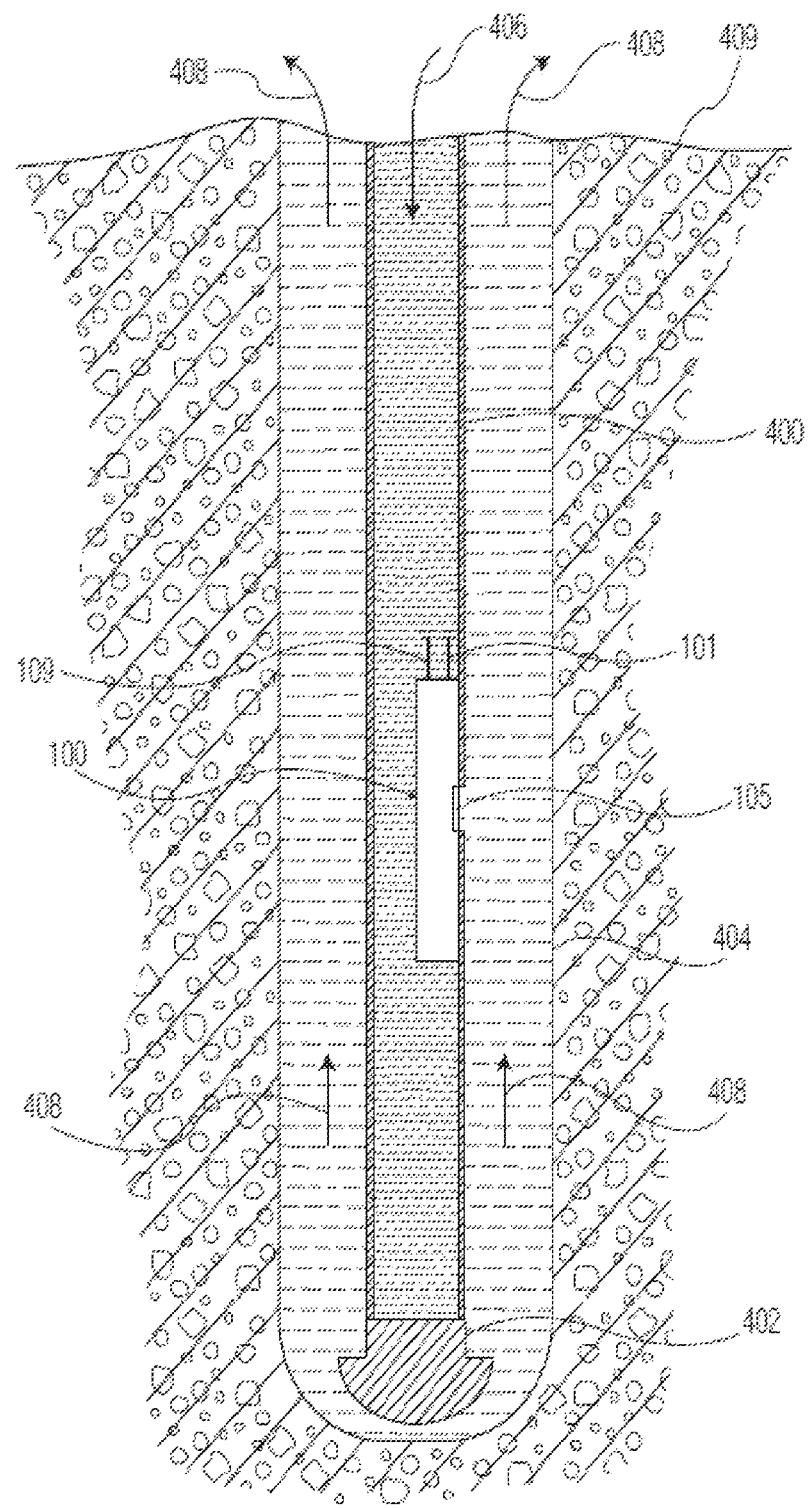
FIG. 12 shows a cutaway view of the device of FIG. 9 rigidly installed in a drill pipe assembly for the first embodiment of the invention.

In FIG. 12, MIR sensor apparatus 100, as described above, is shown secured within a drill pipe assembly 400 proximate a drill bit 402 within a well borehole 404. The sensor apparatus 100 is close to but far enough above drill bit 402 to avoid excessive vibration. A distance ranging 10 to 30 feet may be required. Newly introduced drilling mud 406 is pumped into the drill pipe assembly 400, and exits from or near drill bit 402 into the borehole 404 space outside the drill pipe assembly 400. The returning drilling mud 408 is forced out of the borehole 404, as shown, and returned to the surface 409. A portion of the returning drilling mud 408 passes over waveguide 105, for continuous or periodic sampling for hydrocarbons, as described briefly above relative to FIG. 10, and in greater detail below. Signal line 109 extend to the surface 409 to transmit spectra signals for analysis.

Figure 13:
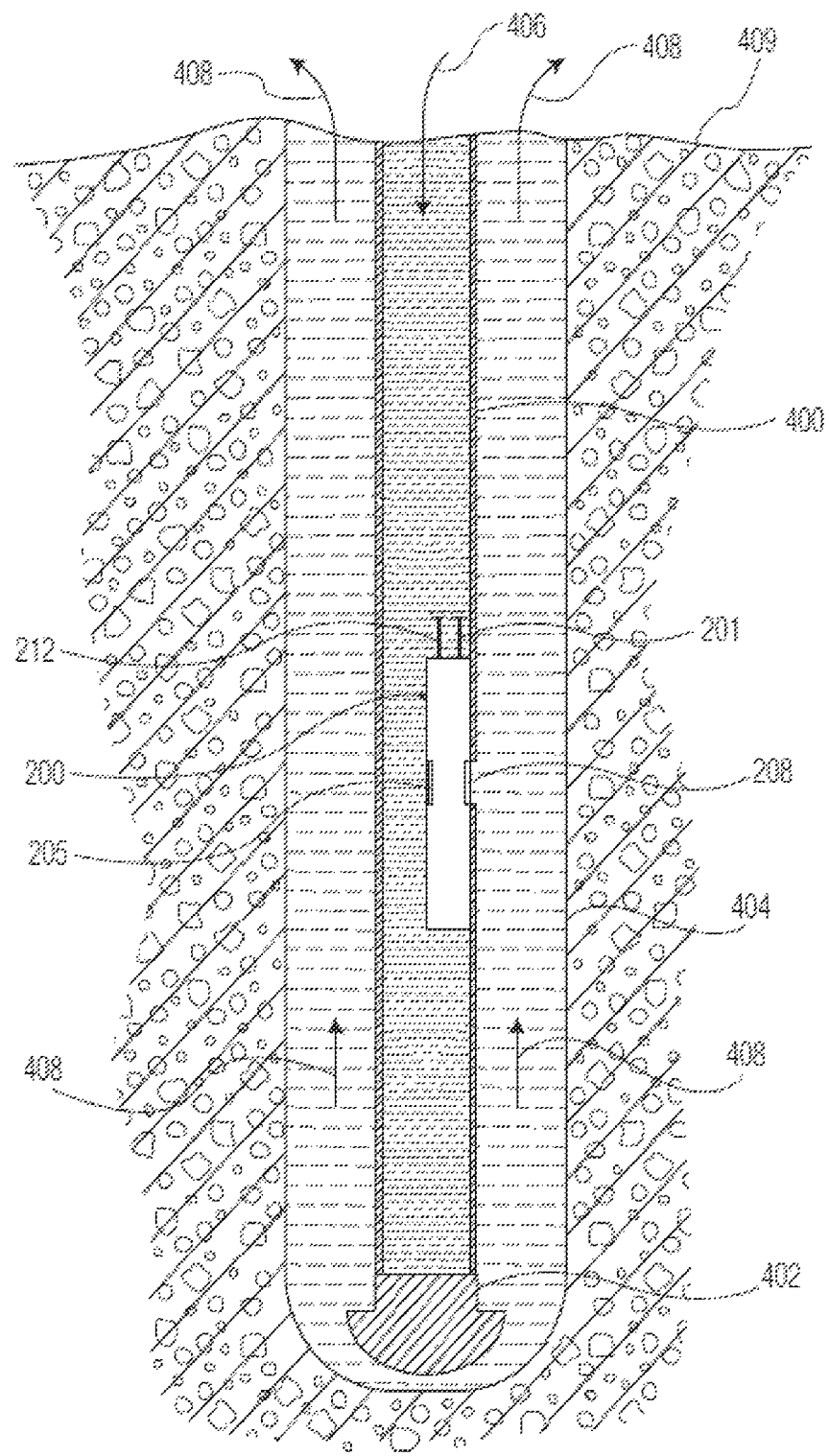
FIG. 13 shows a cutaway view of the device of FIG. 10 rigidly installed in a drill pipe assembly for a second embodiment of the invention.

In FIG. 13, MIR sensor apparatus 200, as described above, is shown secured within a drill pipe assembly 400 proximate a drill bit 402 within a well borehole 404. Sensor apparatus 200 is secured as close to drill bit 402 as possible, but at a position free of excessive vibration produced during drilling (about 10 to 30 feet, for example). As described above, sensor apparatus 200 samples newly introduced drilling mud passing over waveguide 205, and returning drilling mud 408 passing over waveguide 208. Signal line 212 extends to the surface to transmit spectra signals for analysis.

Note that the device 100 is typical for use as a wireline lowered bore-hole analyzer and should be no greater than 4 inches in diameter. Device 200 will preferably fit within the thickness of a drill pipe so its width is much narrower (conventionally 1-2 cm). Length is not critical for either device, and can extend from four feet to over six feet, for example.

The optical fibers 104 and 106 of device 100, and 204, 206, 207, 209 of device 200, are IR optical fibers (usually 300-1000 μm in diameter at various lengths) made from material such as chalcogenides, silver halides, sapphire, for example. The Planar thin-film waveguides 105 of device 100, and 205 and 208 of device 200 can be made from GaAs/AlGaAs. GaAs/AlGaAs are ideally compatible with and tailored to QCL emissions.

The detector controllers 108 and 211 of devices 100 and 200, respectively, are programmed to use known multivariate data analysis (chemometrics) using Eigenvector-based methods for evaluating (i) overlapping spectral signatures, and (ii) for quantitatively discriminating variations of the target analyte concentrations from background fluctuations and drifts. These algorithms have already been implemented for unattended operation of mid-infrared chemical sensor systems. Chemometric algorithms, and in particular principal component analysis/regression (PCA/PCR) and partial least squares (PLS) techniques are ideally suited to address the data processing for devices 100 and 200.

Figure 14:
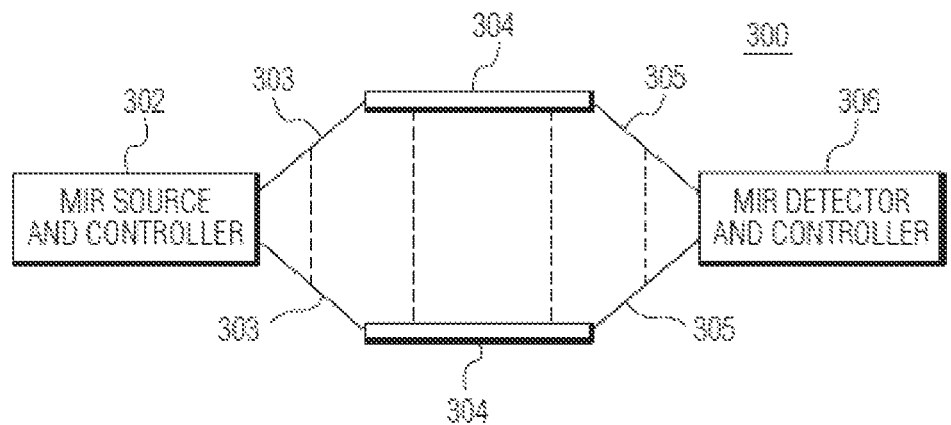
FIG. 14 shows a simplified block schematic diagram of a well logging device or tool that includes a plurality of waveguides that can be individually selected for use at any given time.

With reference to FIG. 14, an extension of the embodiment of the invention of FIG. 10 is shown. The extension includes the use of a plurality of juxtaposed waveguides 304. An MIR source and controller 302 provides MIR light rays that are conveyed or carried by optical fibers or cables 303 to the plurality of waveguides 304, respectively. Modulated light signals emitted from the plurality of waveguides 304, as previously described for the device of FIG. 11 that includes a single waveguide 205, are conveyed or carried by a plurality of optical fibers or cables 305, respectively, to an MIR detector and controller 306 for processing to derive the spectra from each of the received light rays for transmission to the surface, as will be described in further detail below. Also, as described further below, the device or system 300 can be readily designed in various embodiments of the invention for operating with just a single waveguide 304 at any given time, whereby if the waveguide becomes defective, it can be replaced by an operable one of the other plurality of waveguides 304. Also, as will be described below, the system 300 can be otherwise configured for coating each of the waveguides 304 with a different polymer or polymer combination to optimize detection of particular different analyte spectra of interest, whereby each of the plurality of waveguides 304 are operable at the same time.

Figure 15:
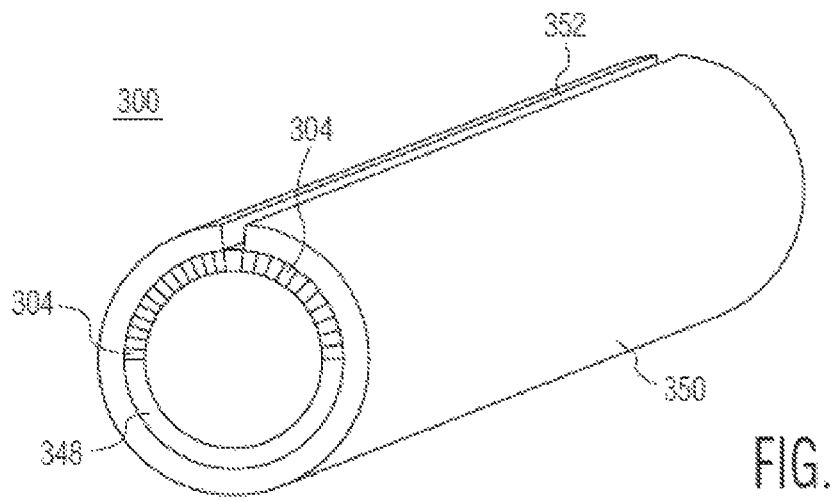
FIG. 15 shows a simplistic mechanical configuration for the embodiment of the invention of FIG. 14.

In FIG. 15, a simplistic mechanical configuration for the embodiment of the invention of FIG. 14 is shown. The plurality of waveguides 304 is juxtaposed within a circular housing 348. The housing is enclosed by a rotatable sleeve 350, with the sleeve 350 including a longitudinal open channel or slotway 352, whereby the collar 350 is rotatable for exposing a desired one of the waveguides 304. If one of the waveguides 304 becomes defective, a user merely has to rotate the collar 350 to expose an operable waveguide 304, to permit reduced downtime due to repair. Note that the materials for the housing 348 and collar 350 can be selected from any suitable corrosion resistant material, such as stainless steel.

Figure 16:
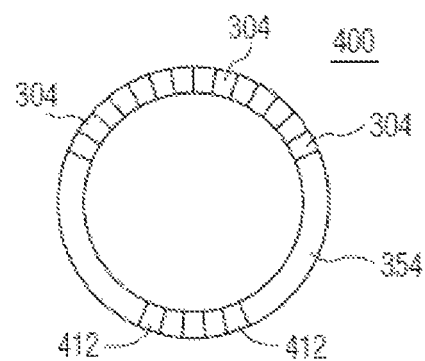
FIG. 16 shows a simplistic mechanical view of yet another embodiment of the invention that is an extension of the embodiment of the invention of FIG. 11.

As shown in FIG. 16, another embodiment of the invention, which is an extension of the embodiment of FIG. 11, includes a circular housing 354, in this example, in which are mounted a plurality of juxtaposed waveguides 304 in one portion, and in an opposing portion a plurality of juxtaposed reference signal waveguides 412, for example. For this configuration, as will be described in further detail below, both electrical and optical switching means are utilized for selecting the ones of the waveguides 304, and 412 that are to be operable at any given time. It is important to note that the mechanical configuration of FIGS. 15 and 16 are given for purposes of example only, and are not meant to be limiting.

Figure 17:
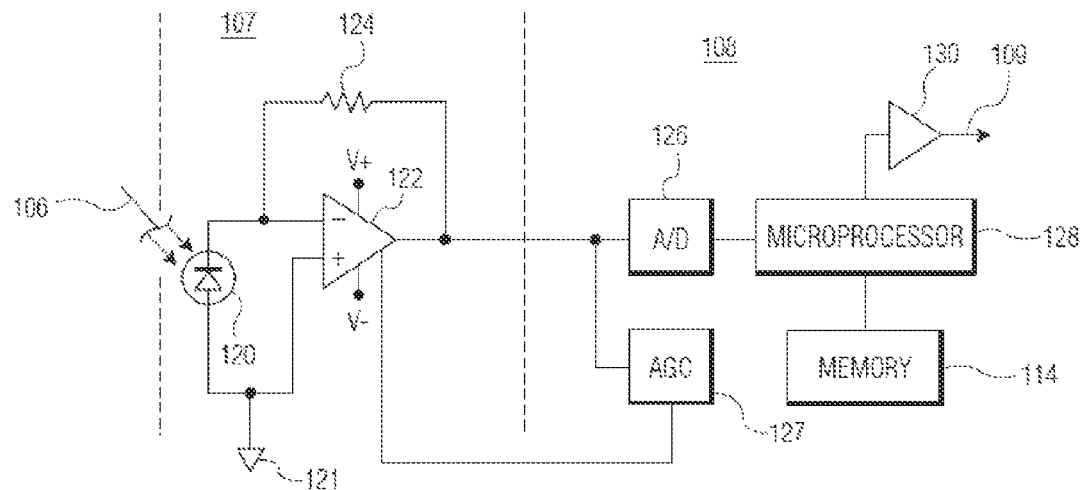
FIG. 17 shows a block circuit schematic diagram of the detector, controller, and memory modules of the embodiment of the invention of FIG. 10.

In FIG. 17, a block schematic circuit diagram is shown to provide further details of the detector 107, and controller 108. The controller 108 includes an automatic gain control (AGC) 127 for maintaining the signal levels from operational amplifier 122 of detector 107. Note that the circuit schematic does not include the MIR source 102 and controller 103, but it is expected that known QCL MIR sources and QCL controllers, available off-the-shelf or in modified form, are preferred for use in the various embodiments of the invention, as previously mentioned above. Returning to FIG. 17, the modulated light ray or wave emitted from waveguide 105 is conveyed by optical fiber or cable 106 to detector 107. In this example, detector 107 includes a photodiode 120 that is responsive to the modulated light ray from optical fiber or cable 106 for producing an electrical current that is detected by operational amplifier 122. As shown, operational amplifier 122 includes a feedback resistor 124, and is powered by the positive DC voltage, V+, and negative DC voltage, V−. Also, the anode of photodiode 120 and non-inverting terminal of operational amplifier 122 are connected in common to a source of reference potential 121, typically ground. The modulated electrical output signal from detector 107 is connected to an analog-to-digital converter 106, for converting the analog modulated electrical signal into a digital output signal that is fed to a microprocessor 128. The microprocessor is programmed to process the data signal it receives into a spectra signal, which is fed both to a memory 114, and to an amplifier 130, the output of which is fed to signal wire 109 for transmitting the processed spectra signal to the surface 409 for analysis or review. The controller 108 can be operated by means not shown to permit the processed spectra signal to be both stored in memory 114 and transmitted via signal wire 109 to the surface 409, or to only transmit the spectra to surface, or to only store the spectra in memory 114 for later use. This example of a detector 107 and controller 108 is not meant to be limiting, but is given for purposes of example.

Figure 18:
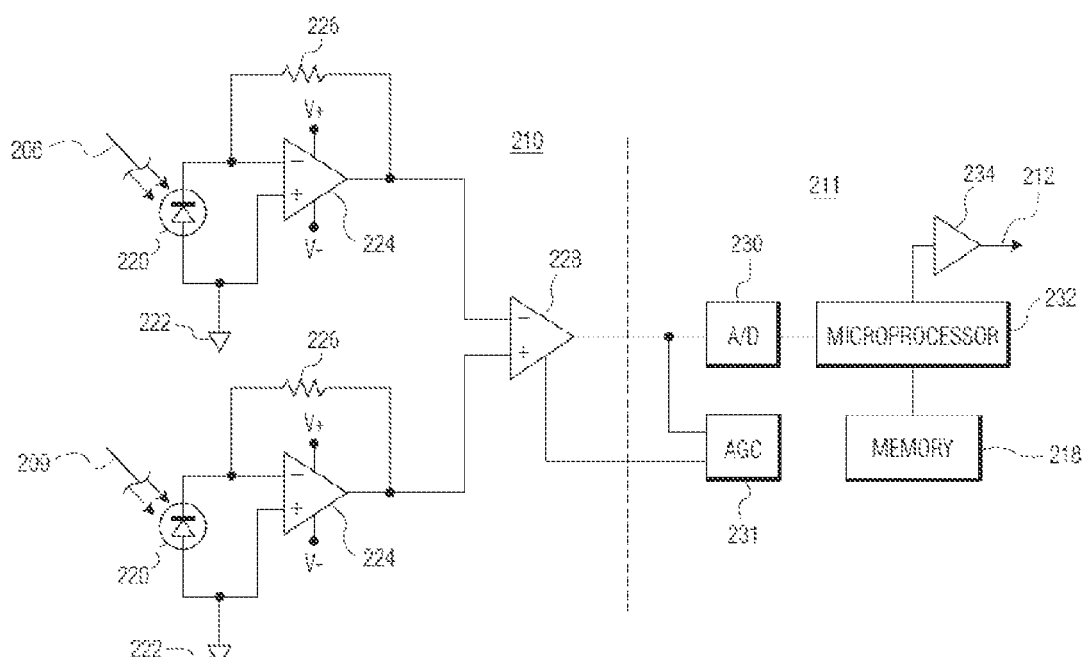
FIG. 18 shows a simplistic block schematic circuit diagram of the detector, controller, and memory of the embodiment of the invention of FIG. 11.

With reference to FIG. 18, a block circuit schematic diagram is shown for providing an example of a detector 210 and controller 211 for the embodiment of the invention of FIG. 11. In this example the controller 211 is provided with an AGC system 231 for maintaining desired output signal levels from differential amplifier 228. As shown, the detector 210 includes a first auto detector circuit including a photodiode 220, operational amplifier 224 with a feedback resistor 226, whereby the photodiode 220 is receptive of a modulated light ray or signal from optical fiber cable 206, for converting the same into an electrical signal that is outputted from amplifier 224 for connection to an inverting terminal of differential amplifier 228. A second photodetector circuit also includes a photodiode 220, operational amplifier 224 with a feedback resistor 226, as shown. In this circuit, the photodiode 220 is receptive of a modulated light signal or ray from optical fiber 209, for converting the same into a modulated electrical signal that is outputted from the associated amplifier 224 for connection to the non-inverting terminal of differential amplifier 228. This latter modulated electrical signal is a reference signal obtained from drilling mud 406 being fed to a drill bit 402, as described relative to FIG. 13. The signal at the non-inverting terminal of differential amplifier 228 is representative of the spectra detected from drilling mud 408 that includes particles, hydrocarbons, and so forth derived during the drilling process, as previously explained. The output signal from differential amplifier 228 is free of common mode signal portions between the reference signal applied to the inverting terminal being subtracted from the sample signal applied to the non-inverting terminal of amplifier 228. As previously described, the use of common mode signal extraction enhances the detection of trace amounts of various hydrocarbons in water, in this example. The analog-to-digital converter 230 converts the analog output signal from amplifier 228 into a digital signal that is fed to microprocessor 238. Microprocessor 232 is programmed to process the digital data signal to provide the associated spectra signal or signals detected, and selectively feed the same via amplifier 232 to the surface 409 on signal line 212, and/or to memory 218.

Figure 19:
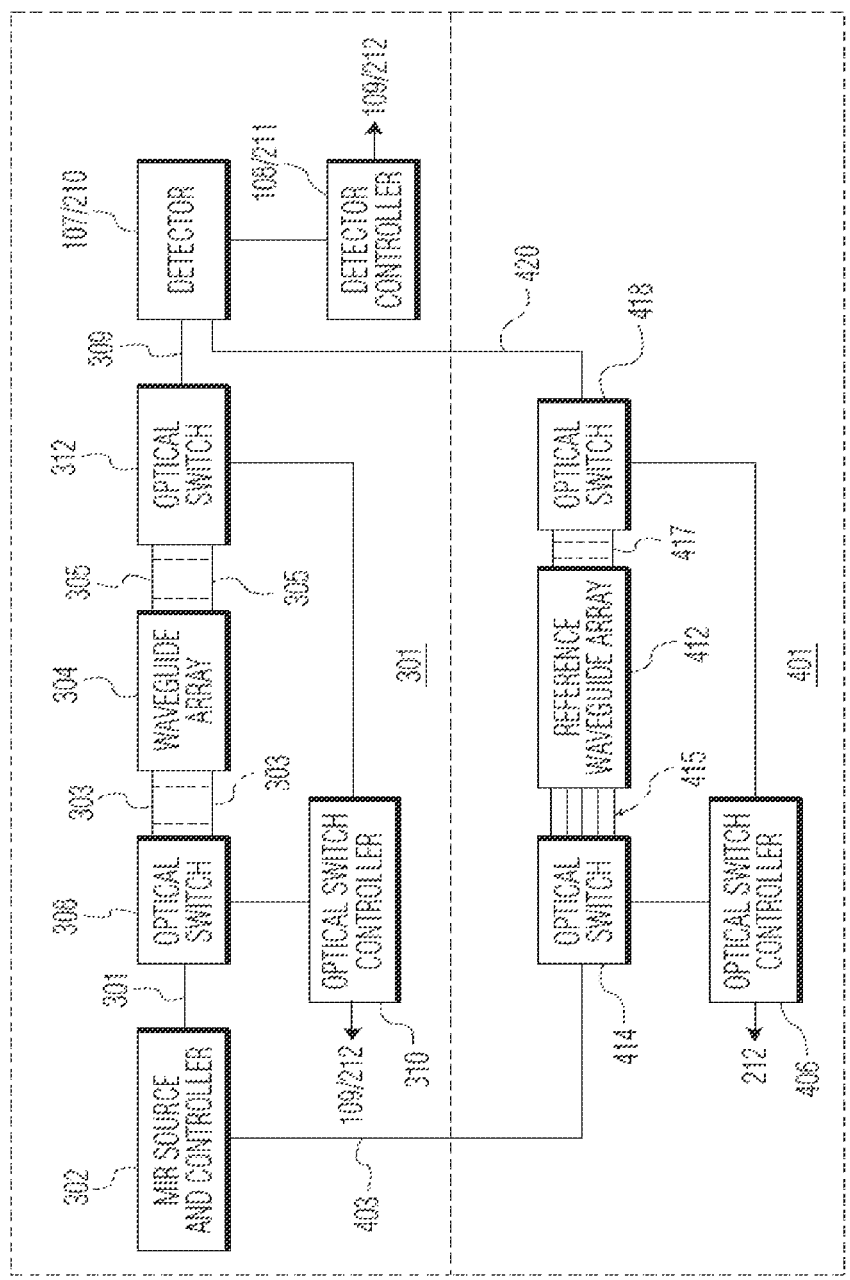
FIG. 19 is a simplistic block diagram of an alternative embodiment in one portion of the invention of FIGS. 10 and 15, and in combination with another portion thereof is an extension of the embodiment of the invention of FIGS. 11 and 16.

In FIG. 19, a simplified block schematic diagram is shown for providing non-mechanical means for selecting for operation individual ones of a waveguide array 304 of a plurality of waveguides. More specifically, MIR source and controller 302 provides an MIR light ray or light wave to an optical switch 308 that is controlled by an optical switch controller 310 receptive of control signals from signal line 212. The optical switch controller is operable for controlling the optical switch 308 to selectively connect the MIR light ray 301 to one of a plurality of optical fibers 303 connected individually to an input end of the plurality of waveguides of waveguide array 304, respectively. A plurality of optical fibers or cables 305 are individually connected to the output side of individual ones of the plurality of waveguides of the waveguide array 304, respectively. Another optical switch 312 controlled by the optical switch controller 310 is operated to connect the active one of the optical fibers 305 to an output optical fiber 309. The modulated optical signal is carried by optical fiber 309 to the input of a detector 107, the latter providing a modulated electrical output signal to controller 108, as previously described.

The circuitry of FIG. 19 can be extended as shown to include a second portion 401, in addition to the first portion 301 as previously described, for permitting operation of the device or system 400 of FIG. 16, in this example. More specifically, another optical switch 414 is provided, that is controlled by an optical switch controller 406 receptive of control signals from signal line 212, for selecting an individual one of a plurality of optical fibers 415, to connect the MIR light ray to a selected input of one of the waveguides 412. The modulated output signal from the operable one of the waveguides 412 are connected by a plurality of optical fibers or cables 417 to an optical switch 418 that is controlled by the controller 406 to connect the output of the active waveguide 412 to an optical fiber or cable 420 for connecting the modulated lightwave to an input of detector 210, in this example. Detector 210 operates as previously described. The output of detector 210 is connected to a controller 211, as previously described, for outputting a processed spectra signal onto signal line 212, all as previously described.

Figure 20:
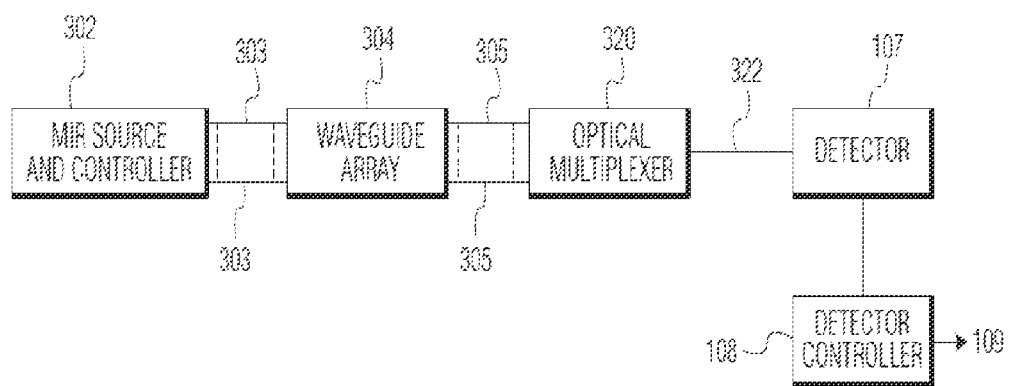
FIG. 20 shows a simplistic block schematic diagram of an alternative embodiment and extension of the embodiment of the invention of FIGS. 10 and 15.

Note that for each embodiment of the invention, the waveguides used can each be coated with a selected polymer or combination of polymers to enhance the detection of a desired spectrum for a hydrocarbon of specific interest. In yet another embodiment of the invention as shown in FIG. 20, the MIR source and controller 302 provides an MIR light ray via a plurality of individual optical fibers or cables 303 to an input side of each one of a plurality of waveguides in a waveguide array 304, thereby activating each one of the waveguides simultaneously. The modulated light ray output signals from each one of the waveguides of the array 304 are carried by a plurality of optical fiber or cables 305 to individual inputs of an optical multiplexer 320. The optical multiplexer multiplexes the modulated optical signals and applies them serially and in spaced apart relationship into an optical fiber or cable 322 for inputting into a detector 107, in this example. Detector 107 is operable as previously described for converting the multiplexed optical signals into modulated electrical signals that are fed to a detector controller 108 for processing as previously described to produce a plurality of multiplexed spectra signals onto signal line 109 for transmission to the surface 409. The embodiment of FIG. 20 can be extended to include subsystem 401 of FIG. 19, whereby the detector would then be detector 210 described above, and the detector controller will be 212 as described above, thereby permitting the inclusion of a common mode signal from an active reference waveguide, as previously described.

Figure 21:
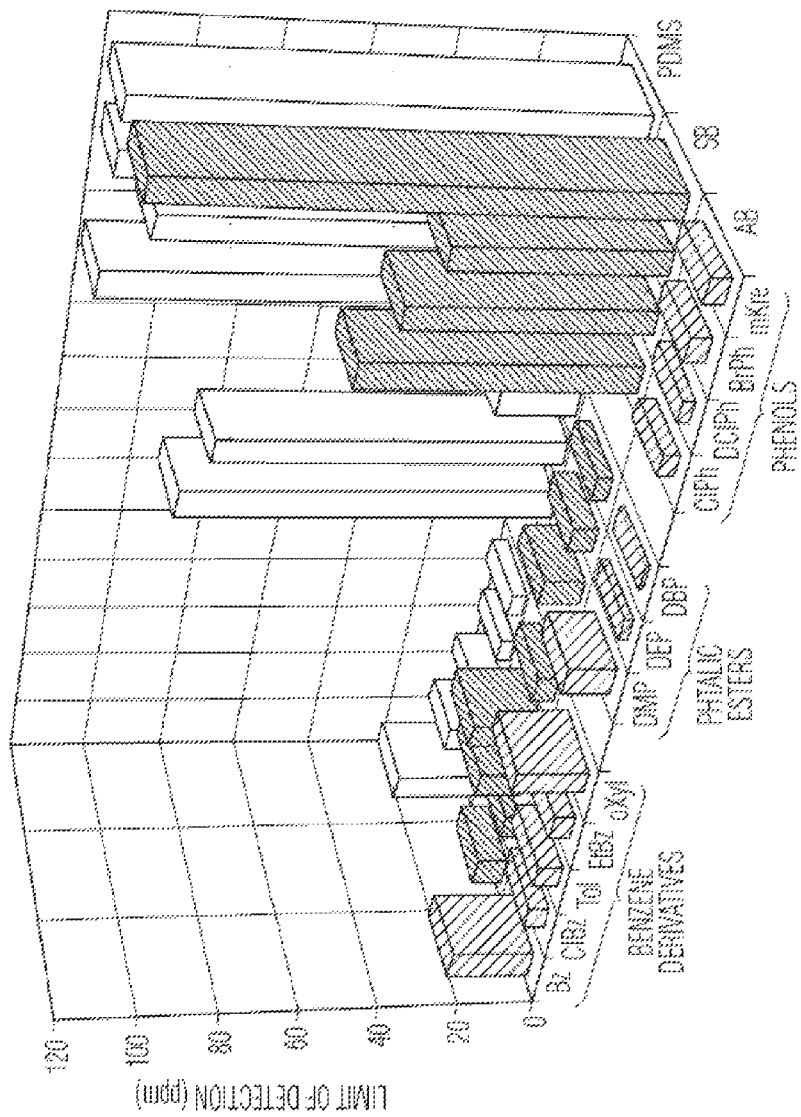
FIG. 21 is a graphical representation showing estimated detection limits for various polymer coatings on a waveguide relative to the detection of benzene derivatives, phthalic esters, and phenols.

FIG. 21 shows a graphical representation of the limits of detection (LOD) in parts per million for detecting various benzene derivatives, phthalic esters, and phenols, relative to three different polymer coatings, namely, AB, SB, and PDMS, as shown in FIG. 21. The polymer coatings are applied in thin layers onto individual but identical waveguides, which in this example were ZnSe-ATR crystals. The polymer layer thickness for polymers AB and SB were about five micrometers, and for the polymer PDMS was about seven micrometers.

For the embodiment of the invention of FIGS. 10 through 20, all of the associated devices are expected to be operated in a continuous mode. However, depending upon a particular application and/or characteristics of the devices used, all or a portion of the devices illustrated may be operated in a continuous or pulsed mode. Regardless, of the operational mode, it may be necessary to interrupt such operation for performing calibration, cleaning, and/or regeneration cycles as determined from operating experiences. For example, drilling mud passing over any of the waveguides of various embodiments of the invention may after long periods of operation begin to adhere to the waveguides, necessitating cleaning of the waveguides. However, as is known in the art, baseline drifts can be automatically compensated through use of polynomial functions continuously monitoring a signal baseline relative to actual output or spectra signals being received at a given time. In this manner, long terms drifts due to drilling mud adhering a waveguide can be automatically compensated, thereby reducing downtime caused by cleaning cycles. Also, as previously mentioned, the surfaces of the waveguides can be coated with relatively transparent low coefficient of friction materials to reduce drilling mud adherence problems.

Although various embodiments of the invention have been shown and described, they are not meant to be limiting. Those of skill in the art may recognize various modifications to these embodiments, which modifications are meant to be covered by the spirit and scope of the appended claims.

What is claimed is:

1. Mid-infrared (MIR) spectrometer apparatus for determining the concentration of hydrocarbon components in aqueous colloidal suspensions of drilling mud being returned to the surface within an oil well borehole as drilling progresses, said apparatus comprising:
    a light source operable for emitting MIR light rays at an output port;
    a first detecting waveguide having a light ray receiving end receptive of said MIR light rays from said light source, an opposing light ray emitting end, and a top face positioned for exposure to and wetting by returning drilling mud;
    at least a first reference waveguide having a light ray receiving end receptive of said MIR light rays from said light source, an opposing light ray emitting end, and a top face positioned for exposure to and wetting by drilling mud being pumped to a drill bit;
    said first detecting waveguide being operable for responding to the MIR light ray(s) from said MIR light source by generating an evanescent wave proximate its top face, said evanescent wave reacting with molecules of interest in said returning drilling mud, thereby producing a modulated MIR light ray(s) at its light ray emitting end;
    said first reference waveguide being operable for responding to the MIR ray(s) from said MIR light source by generating an evanescent wave reacting with molecules of said drilling mud being pumped to said drill bit, thereby producing a modulated MIR light ray at its light ray emitting end;
    a MIR light ray detector including:
    first converter means responsive to modulated MIR light rays from said first detecting waveguide, for converting the same into a first electrical signal;
    second converter means responsive to modulated MIR light rays from said first reference waveguide, for converting the same into a second electrical signal; and
    means for subtracting said second electrical signal from said first electrical signal, for producing an output signal free of common mode signals and/or noise therebetween; and
    processor means receptive of said common mode free output signal from said MIR hg ray detector, for processing the same to extract spectra signals therefrom for identifying the concentration of related hydrocarbon components in said returning drilling mud.

2. The apparatus of claim 1, further including a housing consisting of corrosion, high impact, and abrasive resistant material for enclosing said MIR light source, said first detecting waveguide with its top face exposed on one side of said housing, said first reference waveguide with its top face exposed on an opposing side of said housing, said first and second light ray detector means, and said processor means, said housing being rigidly installed in a wall of a drill pipe assembly proximate a drill bit within an oil well borehole, with the top face of said first reference waveguide being exposed within the drill pipe assembly in the pathway of newly introduced drilling mud, and with the top face of said first detecting waveguide being exposed and located within the pathway of returning drilling mud flowing toward the surface within the associated borehole between said drill pipe assembly and an inside wall of said borehole.

3. The apparatus of claim 1, further including:
    first optical fiber means connected between the output port of said MIR light source and the light ray receiving end of said first detecting waveguide, for carrying said MIR light rays thereto; and
    second optical fiber means connected between the output port of said MIR light source and the light ray receiving end of said first reference waveguide, for carrying said MIR light rays thereto.

4. The apparatus of claim 3, further including:
    third optical fiber means connected for carrying modulated light rays from the light ray emitting end of said first detecting waveguide to said first converter means; and
    fourth optical fiber means connected for carrying modulated light rays from the light ray emitting end of said first reference waveguide to said second converter means.

5. The apparatus of claim 1, further including a signal line connected between said processor means and the surface, for conducting processed spectra signals for analysis at the surface while drilling progresses.

6. The apparatus of claim 1, wherein said processor means further includes memory means for storing said spectra signals for later analysis.

7. The apparatus of claim 1, further including a signal line connected between said processor means and the surface, for conducting processed spectra signals for analysis at the surface while drilling progresses, said processor means further including memory means for storing the processed spectra signals.

8. The apparatus of claim 7, wherein said processor means further includes means for selectively providing said spectra signals only on said signal line, or only for storage in said memory means, or both on said signal line and for storage in said memory means.

9. The apparatus of claim 1, further including a hydrophobic polymer coating on the top faces of each of said first detecting and first reference waveguides.

10. The apparatus of claim 1, further including a diamond-like antiabrasive coating on the top faces of each of said first detecting and first reference waveguides.

11. The apparatus of claim 1, further including a hydrophobic polymer coating on the top face of said first detecting waveguide for enhancing the detection of spectra of a particular hydrocarbon of interest.

12. The apparatus of claim 1, further including:
    a plurality of detecting waveguides;
    a signal line connected from the surface to the processor means, for providing spectra signals to the surface for analysis as drilling progresses, and for providing control signals from the surface to said processor means; and
    first optical switching means responsive to control signals for both connecting one of said plurality of detecting waveguides between said MIR light source and detector, and for removing a said one of said plurality of detecting waveguides should it become defective, and substituting therefor an operable one of said plurality of detecting waveguides.

13. The apparatus of claim 12, wherein said first optical switching means includes:
a first optical switch between said MIR light source and the light ray receiving ends of said plurality of detecting waveguides;
a second optical switch between light ray emitting ends of said plurality of detecting waveguides and said detector; and
a first optical switch controller responsive to control signals for operating said first and second optical switches to select one of said plurality of detecting waveguides for operation between said MIR light source and said detector.

14. The apparatus of claim 13, further including:
a plurality of reference waveguides; and
second optical switching means responsive to control signals for both connecting one of said plurality of reference waveguides between said MIR light source and said detector, and for removing said one of said plurality of reference waveguides should it become defective, and substituting therefor an operable one of said plurality of reference waveguides.

15. The apparatus of claim 14, wherein said second optical switching means includes:
a third optical switch located between said MIR light source and light receiving ends of said plurality of reference waveguides;
a fourth optical switch located between light ray emitting ends of said plurality of reference waveguides and said detector; and
a second optical switch controller responsive to control signals for operating said third and fourth optical switches to select an operable one of said reference waveguides.

16. The apparatus of claim 14, further including a hydrophobic polymer coating on top faces of each one of said plurality of reference waveguides, respectively.

17. The apparatus of claim 16, wherein said hydrophobic polymer is selected from the group consisting of Teflon AF, PDMS, PIB, E/Pco, PSB, LDPE, PBCT, PAB, PA, PDMS/DVBS, and Carbowax/DVB.

18. The apparatus of claim 14, wherein said plurality of reference waveguides are made from material selected from the group consisting of ZnSe, ZnS, KRS, and Ge.

19. The apparatus of claim 14, further including an antiabrasive protective coating on each one of said plurality of reference waveguides.

20. The apparatus of claim 19, wherein said protective coating consists of a diamond-like coating.

21. The apparatus of claim 12, further including a hydrophobic polymer coating on top faces of each one of said plurality of detecting waveguides.

22. The apparatus of claim 21, wherein said hydrophobic polymer is selected from the group consisting of Teflon AF, PDMS, PIB, E/Pco, PSB, LDPE, PBCT, PAB, PA, PDMS/DVBS, and Carbowax/DVB.

23. The apparatus of claim 21, wherein said protective coating consists of a diamond-like coating.

24. The apparatus of claim 12, wherein said plurality of detecting waveguides are made from material selected from the group consisting of ZnSe, ZnS, KRS, and Ge.

25. The apparatus of claim 12, further including an antiabrasive protective coating on top faces of each one of said plurality of detecting waveguides, and each one of said plurality of reference waveguides.

26. The apparatus of claim 25, wherein said protective coating consists of a diamond-like coating.

27. The apparatus of claim 1, further including:
a plurality of detecting waveguides each having a top face, a light receiving end, and a light emitting end;
a coating on each of the top faces of said plurality of detecting waveguides for enhancing detection of spectra of different hydrocarbons of interest, respectively;
optical fiber means for directing MIR light rays from said MIR light source to the light ray receiving ends of each of said plurality of detecting waveguides; and
an optical multiplexer receptive of modulated MIR light rays from the individual light ray emitting ends of said plurality of detecting waveguides, respectively, for providing a multiplexed output signal of said modulated light rays to said detector.

28. The apparatus of claim 1, wherein said first detecting waveguide and said first reference waveguide each are made from material selected from the group consisting of ZnSe, ZnS, KRS, and Ge.

29. The apparatus of claim 1, wherein:
said subtracting means includes a differential comparator having an inverting input terminal, a non-inverting input terminal, and an output terminal at which said common mode free output signal is provided;
said first converter means includes both a photodiode for converting the light rays from said first detecting waveguide into said first electrical signal and an amplifier for amplifying the first electrical signal for application to the non-inverting input terminal of said differential comparator; and
said second converter means includes both a photodiode for converting the light rays from said first reference waveguide into said second electrical signal, and an amplifier for amplifying the second electrical signal for application to the inverting input terminal of said differential comparator.

30. The apparatus of claim 29, wherein said processor means includes:
an A/D converter receptive of said common mode output signal for converting the same into a digital signal; and
a microprocessor programmed for processing said digital signal to extract said spectra signals.

31. The apparatus of claim 30, wherein said processor means further includes a memory, said microprocessor being further programmed to either apply said spectra signals to an output signal line for sending said spectra signals to the surface for analysis, or to said memory for later analysis, or both to said output signal line and to said memory.

32. The apparatus of claim 30, wherein processor means further includes an automatic gain control for maintaining the output signal level from said differential comparator.

33. The apparatus of claim 1, wherein said MIR light source is selected for emitting light rays in a spectral range from 2.5 µm to 25 µm.

34. The apparatus of claim 33, wherein said MIR light source consists of a quantum cascade laser.

35. Mid-infrared (MIR) spectrometer apparatus for determining the amount of hydrocarbon components dissolved, emulsified, or entrained in an aqueous colloidal suspension, comprising:
a source of MIR light rays having an output port;
at least a first waveguide having a light ray receiving end, an opposing light ray emitting end, a top face for exposure to and wetting by a colloidal suspension of interest, and a bottom face;

first optical fiber means positioned for carrying MIR light rays from the output port of said MIR light source to said light ray receiving end of said first waveguide;

a light ray detector having an input port and an output port;

second optical fiber means positioned for carrying modulated MIR light rays from the light ray emitting end of said waveguide to said input port of said light ray detector;

said first waveguide being operable for responding to a MIR light ray from said MIR light source by generating an evanescent wave proximate its top face, said evanescent wave reacting with molecules of interest in said colloidal suspension thereby producing a modulated MIR light ray at its light ray emitting end;

said light ray detector being operable for converting said modulated MIR light ray into an electrical signal at its output port;

an output signal line;

processor means connected to said output port of said light ray detector, for processing said electrical signal to extract spectra signals therefrom for identifying the concentration of related hydrocarbon components in the colloidal suspension, said spectra signals being provided on said output signal line;

heat resistant electrical insulative material being configured to encase said MIR light source, first and second optical fiber means, detector, and processor means; and a housing consisting of corrosion resistant high impact and abrasive resistant material for rigidly containing therein said heat resistant electrical insulative material, a window in a portion of said housing securely retaining said first waveguide with its front face exposed for receiving said aqueous colloidal suspension, and its bottom face secured to said insulative material, said output signal line extending from said housing.

36. The apparatus of claim 35, further including memory means for receiving and storing said spectra signals from said processor means, said memory means being encased within said insulative material.

37. The apparatus of claim 35, further including means for positioning said housing proximate a drill bit within an oil well borehole where returning drilling mud will pass over the front face of said waveguide, for sampling the spectra of hydrocarbons in the mud.

38. The apparatus of claim 35, further including:
a plurality of waveguides installed in juxtaposition to one another in said housing, each having a top face exposed from an outside wall of said housing; and
means for both selecting an individual operable one of said plurality of waveguides for operation, and for changing the selected one in the even it becomes inoperable to another operable one of said plurality of waveguides.

39. The apparatus of claim 38, wherein said selecting means includes a rotatable collar installed on said housing, said collar including a longitudinal open channel, for permitting the collar to be rotated to a position for exposing a top face of a selected one of said plurality of waveguides.

40. The apparatus of claim 38, further including a hydrophobic polymer coating on the top faces of each of said plurality of waveguides.

41. The apparatus of claim 40, wherein said hydrophobic polymer is selected from the group consisting of Teflon AF, PDMS, NB, E/Pco, PSB, LDPE, PBCT, PAB, PA, PDMS/DVBS, and Carbowax/DVB.

42. The apparatus of claim 40, further including a layer of antiabrasive material on top of said hydrophobic polymer coatings on said plurality of waveguides.

43. The apparatus of claim 42, wherein the antiabrasive material consists of DLC.

44. The apparatus of claim 38, further including a layer of antiabrasive material on the top faces of each of said plurality of waveguides.

45. The apparatus of claim 35, further including a hydrophobic polymer coating on the top face of said first waveguide for enhancing the detection of hydrocarbon components.

46. The apparatus of claim 45, wherein said hydrophobic polymer is selected from the group consisting of Teflon AF, PDMS, PM, E/Pco, PSB, LDPE, PBCT, PAB, PA, PDMS/DVBS, and Carbowax/DVB.

47. The apparatus of claim 45, further including a DLC coating on top of said hydrophobic polymer coating.

48. The apparatus of claim 35, wherein said first waveguide consists of material selected from the group consisting of ZnSe, ZnS, KRS, and Ge.

49. The apparatus of Claim 35, further including a layer of antiabrasive material on the top face of said first waveguide.

50. The apparatus of claim 49, wherein said antiabrasive, materials consists of a diamond-like coating (DLC).

51. The apparatus of claim 35, wherein said light ray detector includes:
a photodiode responsive to said modulated MIR light ray for converting it into an electrical signal; and
an amplifier receptive of the electrical signal for amplifying and providing it at said output port.

52. The apparatus of claim 51, wherein said processor means includes:
an AD receptive of the amplified electrical signal for converting it into a digital signal;
a memory; and
a microprocessor programmed for processing said digital signal to extract therefrom spectra of said hydrocarbon components, and for selectively inputting the spectra to said memory for storage for later analysis, and/or providing the spectra on said output signal line.

53. The apparatus of claim 35, further including:
a plurality of waveguides installed in juxtaposition to one another in said housing, each having a top face exposed from an outside wall of said housing;
a plurality of hydrophobic polymers each selected for enhancing the response to spectra of different ones of said hydrocarbon components, each being coated on individual ones of said plurality of waveguides, respectively;
said first optical fiber means further including means for conveying MIR light rays from said MIR light source to individual light receiving ends of said plurality of waveguides, respectively; and
an optical multiplexer having a plurality of input ports for receiving a plurality of individual light rays from light emitting ends of said plurality of waveguides, respectively, and an output port for providing a multiplexed optical output signal of said plurality of individual light rays,
said light ray detector being receptive of said multiplexed optical output signal, for converting the same into a multiplexed electrical signal, and
said processor means being responsive to the multiplexed electrical signal, for extracting therefrom spectra signals representative of the concentration of hydrocarbon components detected from the aqueous colloidal suspension.

54. The apparatus of claim 53, further including a coating of antiabrasive material on top of the hydrophobic polymer coatings on said plurality of waveguides, respectively.

55. A method for determining the concentration of hydrocarbon components in aqueous colloidal suspensions of drilling mud being returned to the surface within an oil well borehole as drilling progresses, said method comprising the steps of:

positioning an exposed top face at least a first detecting waveguide for wetting by returning drilling mud from a drill bit;

positioning an exposed top face of at least a first reference waveguide for wetting by new drilling mud being pumped to a drill bit in the borehole;

feeding a MIR light ray from a MIR light source to light receiving ends of each one of said first detecting waveguide and first reference waveguide, thereby causing evanescent waves to be generated from the top faces of the waveguides, respectively, for reacting with molecules of components in the returning and new drilling muds, respectively, thereby causing modulated optical signals to be produced at emitting ends of said first and second waveguides, respectively;

converting the modulated optical signals from said first detecting and first reference waveguides into a first electrical signal, and a second electrical signal, respectively;

subtracting said second electrical signal from said first electrical signal to remove common mode components therebetween, to obtain a common mode free electrical signal; and processing the common mode free electrical signal to extract the spectra signals of the hydrocarbon components in the returning drilling mud.

56. The method of claim 55, further including the step of storing the spectra signals in memory for later analysis.

57. The method of claim 55, further including the step of feeding the spectra signals into an output signal line extending to the surface to permit analysis thereof as drilling progresses.

58. The method of claim 55, further including the steps of coating the top faces of the first detecting and first reference waveguides, respectively, with a hydroscopic polymer to enhance respective evanescent wave interaction with molecules of components in the returning and new drilling muds, respectively.

59. The method of claim 58, further including the steps of applying a coating of antiabrasive material onto the polymer coatings on said first detecting and first reference waveguides, respectively.

60. The method of claim 55, further including the steps of coating the top faces of the first detecting and first reference waveguides, respectively, with an antiabrasive material.

61. A method for determining the concentration of hydrocarbon components in aqueous colloidal suspensions of drilling mud being returned to the surface within an oil well borehole as drilling progresses, said method comprising the steps of:

positioning a plurality of detecting waveguides with top faces exposed to wetting by returning drilling mud;

feeding an MIR light ray from said MIR light source to light receiving ends of each one of said plurality of detecting waveguides, respectively, thereby causing evanescent waves to be generated from the top faces, respectively, for reacting with molecules of hydrocarbon components in the returning drilling mud, respectively, thereby causing modulated optical signals to be produced at emitting ends of each one of said plurality of detecting waveguides, respectively;

selecting at least one modulated optical signal of said plurality of detecting waveguides;

processing the selected one modulated optical signal to extract spectra signals therefrom; and selectively either storing the spectra signals in memory for later analysis, and/or feeding the spectra signals via an output signal line to the surface for analysis as drilling progresses.

62. The method of claim 61, further including the step of coating the top faces of each of said plurality of detecting waveguides with a hydrophobic polymer for enhancing the detection of hydrocarbon components.

63. The method of claim 62, further including the step of coating the hydrophobic polymer coatings on each of said plurality of detecting waveguides with a non-abrasive material.

64. The method of claim 61, further including the step of coating the top faces of each of said plurality of detecting waveguides each with a hydrophobic polymer, respectively, for enhancing the detection of a specific hydrocarbon component, respectively.

65. The method of claim 64, further including the steps of:

multiplexing the modulated optical signals from the emitting ends of said plurality of detecting waveguides; and processing the multiplexed modulated optical signals to extract the spectra signals associated therewith.

66. The method of claim 64, further including the step of coating the hydrophobic coatings on each ones of said plurality of detecting waveguides with a non-abrasive material.

* * * * *